US010413710B2

(12) United States Patent
Lutz et al.

(10) Patent No.: US 10,413,710 B2
(45) Date of Patent: Sep. 17, 2019

(54) PRESSURE REFERENCE ASSEMBLIES FOR BODY FLUID DRAINAGE SYSTEMS AND ASSOCIATED METHODS

(71) Applicants: University of Washington through its Center for Commercialization, Seattle, WA (US); Aqueduct Neurosciences, Inc., Kirkland, WA (US)

(72) Inventors: Barry Lutz, Seattle, WA (US); Samuel R. Browd, Seattle, WA (US); Thomas Clement, Kirkland, WA (US); Brian Cran, Kirkland, WA (US); Joel Relethford, Kirkland, WA (US)

(73) Assignee: University of Washington, Seattle, WA (US)

( * ) Notice: Subject to any disclaimer, the term of this patent is extended or adjusted under 35 U.S.C. 154(b) by 265 days.

(21) Appl. No.: 15/111,459

(22) PCT Filed: Jan. 16, 2015

(86) PCT No.: PCT/US2015/011865
§ 371 (c)(1),
(2) Date: Jul. 13, 2016

(87) PCT Pub. No.: WO2015/109260
PCT Pub. Date: Jul. 23, 2015

(65) Prior Publication Data
US 2016/0331949 A1 Nov. 17, 2016

Related U.S. Application Data

(60) Provisional application No. 61/928,286, filed on Jan. 16, 2014.

(51) Int. Cl.
*A61M 27/00* (2006.01)
*A61B 5/03* (2006.01)

(52) U.S. Cl.
CPC ........... *A61M 27/006* (2013.01); *A61B 5/031* (2013.01); *A61B 5/03* (2013.01); *A61M 2205/3331* (2013.01)

(58) Field of Classification Search
CPC ..... A61M 27/002; A61M 27/006; A61B 5/03; A61B 5/031; A61B 5/032; A61B 5/036
(Continued)

(56) References Cited

U.S. PATENT DOCUMENTS 3,589,363 A 6/1971 Banko
3,769,982 A 11/1973 Schulte
(Continued)

FOREIGN PATENT DOCUMENTS

CN 2421023 Y 2/2001
CN 2614684 Y 5/2004
(Continued)

OTHER PUBLICATIONS

International Search Report and Written Opinion dated Jun. 17, 2015 in International Application No. PCT/US15/11865, 10 pages.
(Continued)

*Primary Examiner* — Philip R Wiest
(74) *Attorney, Agent, or Firm* — Perkins Coie LLP

(57) ABSTRACT

Drainage systems for excess body fluids and associated methods are disclosed herein. A drainage system in accordance with an embodiment of the present technology can include, for example, a drainage catheter, a first reference line, a second reference line, and a pressure sensor assembly. The catheter can include a flexible interface member and an inlet can be placed in fluid communication with a site of excess body fluid within a patient. A first flexible region of the first reference line can be in pressure communication with the flexible interface member, and a second flexible region of the second reference line can be in pressure
(Continued)

communication with the surrounding atmosphere. The pressure sensor assembly can be spaced apart from the flexible regions, and measure the pressures of the first and second reference lines. This information can be used to determine the pressure at the site of excess body fluid.

26 Claims, 9 Drawing Sheets

(58) Field of Classification Search
USPC .......................................................... 604/8, 9
See application file for complete search history.

(56) References Cited

U.S. PATENT DOCUMENTS

| | | | |
|---|---|---|---|
| 3,911,902 A | 10/1975 | Delpy | |
| 3,913,882 A | 10/1975 | Moulet et al. | |
| 3,991,768 A | 11/1976 | Portnoy | |
| 4,156,422 A | 5/1979 | Hildebrandt et al. | |
| 4,206,762 A | 6/1980 | Cosman et al. | |
| 4,601,724 A | 7/1986 | Hooven et al. | |
| 4,653,508 A | 3/1987 | Cosman | |
| 4,658,829 A | 4/1987 | Wallace | |
| 4,741,730 A | 5/1988 | Dormandy, Jr. et al. | |
| 4,923,444 A | 5/1990 | Daoud et al. | |
| 5,291,899 A | 3/1994 | Watanabe et al. | |
| 5,573,007 A | 11/1996 | Bobo et al. | |
| 5,584,314 A | 12/1996 | Bron et al. | |
| 6,241,660 B1 | 6/2001 | Dolle et al. | |
| 6,264,625 B1 | 7/2001 | Rubenstein et al. | |
| 6,295,877 B1 | 10/2001 | Aboul-hosn et al. | |
| 6,336,924 B1 | 1/2002 | Lecuyer et al. | |
| 6,383,160 B1 | 5/2002 | Madsen | |
| 6,481,292 B1 | 11/2002 | Reich et al. | |
| 6,585,677 B2 | 7/2003 | Cowan, Jr. et al. | |
| 6,673,022 B1 | 1/2004 | Bobo et al. | |
| 6,953,444 B2 | 10/2005 | Rosenberg | |
| 7,189,221 B2 | 3/2007 | Silverberg et al. | |
| 7,309,330 B2 | 12/2007 | Bertrand et al. | |
| 8,066,681 B1 | 11/2011 | Hall et al. | |
| 8,109,899 B2 | 2/2012 | Sundstrom et al. | |
| 8,123,714 B2 | 2/2012 | Ludin et al. | |
| 8,192,366 B2 | 6/2012 | Mauge et al. | |
| 8,608,716 B2 | 12/2013 | Schroeter et al. | |
| 8,870,787 B2 | 10/2014 | Yadav et al. | |
| 2003/0139699 A1 | 7/2003 | Rosenberg | |
| 2003/0233143 A1 | 12/2003 | Gharib et al. | |
| 2004/0111079 A1 | 6/2004 | Hayes et al. | |
| 2004/0147871 A1 | 7/2004 | Burnett et al. | |
| 2004/0260229 A1 | 12/2004 | Meir et al. | |
| 2005/0010159 A1 | 1/2005 | Reich et al. | |
| 2005/0020962 A1 | 1/2005 | Reich et al. | |
| 2005/0038371 A1 | 2/2005 | Reich et al. | |
| 2005/0055009 A1 | 3/2005 | Rosenberg et al. | |
| 2005/0182463 A1 | 8/2005 | Hunter et al. | |
| 2005/0187515 A1 | 8/2005 | Varrichio et al. | |
| 2006/0052737 A1 | 3/2006 | Bertrand et al. | |
| 2006/0173419 A1 | 8/2006 | Malcolm et al. | |
| 2006/0220457 A1 | 10/2006 | Yabumoto | |
| 2007/0000333 A1 | 1/2007 | Brugger et al. | |
| 2007/0038171 A1 | 2/2007 | Mayer et al. | |
| 2007/0106209 A1 | 5/2007 | Williams et al. | |
| 2007/0213656 A1 | 9/2007 | Ferdinand | |
| 2008/0139959 A1 | 6/2008 | Miethke et al. | |
| 2009/0005720 A1 | 1/2009 | Ludin et al. | |
| 2009/0036754 A1 | 2/2009 | Pons et al. | |
| 2010/0076366 A1 | 3/2010 | Henderson et al. | |
| 2010/0121250 A1 | 5/2010 | Pizzi et al. | |
| 2010/0298771 A1 | 11/2010 | Tan | |
| 2010/0317977 A1 | 12/2010 | Piaget et al. | |
| 2010/0331813 A1 | 12/2010 | Robinson et al. | |
| 2011/0029050 A1 | 2/2011 | Elefteriades et al. | |
| 2011/0166497 A1 | 7/2011 | Criado et al. | |
| 2011/0275976 A1 | 11/2011 | Negre et al. | |
| 2012/0046596 A1 | 2/2012 | Ludin et al. | |
| 2012/0259265 A1 | 10/2012 | Salehi et al. | |
| 2012/0302938 A1* | 11/2012 | Browd ................ | A61M 27/006 604/9 |
| 2013/0150779 A1 | 6/2013 | Field et al. | |
| 2013/0197422 A1 | 8/2013 | Browd et al. | |
| 2013/0247644 A1 | 9/2013 | Swoboda et al. | |
| 2015/0112289 A1 | 4/2015 | Stebbins et al. | |
| 2016/0067464 A1 | 3/2016 | Kim et al. | |
| 2017/0209056 A1 | 7/2017 | Browd | |
| 2018/0028794 A1 | 2/2018 | Browd | |
| 2019/0126018 A1 | 5/2019 | Browd | |

FOREIGN PATENT DOCUMENTS

| | | |
|---|---|---|
| CN | 1565662 A | 1/2005 |
| CN | 101342402 A | 1/2009 |
| DE | 4130601 | 4/1992 |
| DE | 10100070 A1 | 7/2002 |
| EP | 0982048 | 3/2000 |
| EP | 1512428 | 3/2005 |
| WO | 023860 | 1/2002 |
| WO | 03057016 A2 | 7/2003 |
| WO | 2011081669 A1 | 7/2011 |
| WO | 2011116393 A1 | 9/2011 |
| WO | 2012078861 A2 | 6/2012 |
| WO | 2012166980 A2 | 12/2012 |
| WO | 2015057648 A1 | 4/2015 |
| WO | 2015109260 A1 | 7/2015 |

OTHER PUBLICATIONS

Zhong, J. et al., "Advances in ICP monitoring techniques", Neurological Research, 2003, pp. 25 and 339.
European Examination Report dated Feb. 14, 2017 in European Patent Application No. 11710987.6, 4 pages.
Examination Report dated Feb. 7, 2017 in Canadian Patent Application No. 2793675, 3 pages.
Examination Report dated Nov. 13, 2015 in corresponding Australian Patent Application No. 2011227017, 6 pages.
Examination Report dated Nov. 23, 2015 in corresponding European Patent Application No. 11710987.6, 4 pages.
Final Office Action dated Feb. 11, 2016 in U.S. Appl. No. 13/636,115, 22 pages.
Final Office Action dated Jun. 18, 2014 in corresponding U.S. Appl. No. 13/488,326, 18 pages.
Final Office Action dated May 22, 2015 in corresponding U.S. Appl. No. 13/488,326, 10 pages.
First Chinese Office Action dated Mar. 14, 2014 for CN 201180022356.X.
International Search Report and Written Opinion dated May 18, 2011 for PCT/US2011/029261 filed Mar. 21, 2011.
Non-Final Office Action dated Aug. 3, 2015 in U.S. Appl. No. 13/636,115, 28 pages.
Non-Final Office Action dated Feb. 24, 2017 in corresponding U.S. Appl. No. 14/667,441, 24 pages.
Non-Final Office Action dated Jan. 13, 2016 in U.S. Appl. No. 14/667,441, 28 pages.
Non-Final Office Action dated Mar. 9, 2017 in U.S. Appl. No. 13/488,326, 13 pages.
Non-Final Office Action dated Oct. 21, 2014 in corresponding U.S. Appl. No. 13/488,326, 27 pages.
Non-Final Office Action dated Oct. 24, 2013 in corresponding U.S. Appl. No. 13/488,326, 25 pages.
Office Action dated Oct. 21, 2015 in corresponding Chinese Patent Application No. 201180022356.X, 37 pages.
Restriction Requirement dated Jan. 28, 2015 for U.S. Appl. No. 13/636,115, filed Sep. 19, 2012.
Second Chinese Office Action dated Feb. 3, 2015 for CN 201180022356.X.
Alzheimer's Association. Alzheimer's Disease Facts and Figures. Chicago : Alzheimer's Association, 2010.
Association, H., Learning about hydrocephalus. 2009.

(56) References Cited

OTHER PUBLICATIONS

Bondurant, C.P. and D.F. Jimenez, Epidemiology of cerebrospinal fluid shunting. Pediatr Neurosurg, 1995. 23(5): p. 254-8; discussion 259.
Browd, S.R., et al., Failure of cerebrospinal fluid shunts: part I: Obstruction and mechanical failure. Pediatr Neurol, 2006. 34(2): p. 83-92.
Browd, S.R., et al., Failure of cerebrospinal fluid shunts: part II: overdrainage, loculation, and abdominal complications. Pediatr Neurol, 2006. 34(3): p. 171-6.
Burnett, Mark G., Sonnad, Seema S. and Stein, Sherman C., Screening tests for normal-pressure hydrocephalus: sensitivity, specificity, and cost. Journal of Neurosurgery, Dec. 2006, vol. 105, pp. 823-829.
Cochrane, D, et al., Model for the cost analysis of shunted hydrocephalic children. Pediatric Neurosurgery, 1995, vol. 23, pp. 14-19.
Codman & Shurtleff, Inc. Life NPH. [Online] [Cited: Jul. 29, 2010.] http://www.lifenph.com/faqs.asp.
Drake, J.M. and J.T. Kestle, Determining the best cerebrospinal fluid shunt valve design: the pediatric valve design trial. Neurosurgery, 1998. 43(5): p. 1259-60.
Drake, J.M., J.R. Kestle, and S. Tuli, Cerebrospinal fluid shunt technology. Clin Neurosurg, 2000. 47: p. 336-45.
Drake, J.M., J.R. Kestle, and S. Tuli, CSF shunts 50 years on—past, present and future. Childs Nerv Syst, 2000. 16(10-11): p. 800-4.
Drake, James, et al., Randomized Trial of Cerebrospinal Fluid Shunt Valve Design in Pediatric Hydrocephalus. Neurosurgery, Aug. 1998, vol. 43, pp. 294-303.
Epstein, F., How to keep shunts functioning, or "The impossible dream". Clin Neurosurg, 1985.32: p. 608-31.
European Search Report dated Jun. 26, 2015 in European App. No. 11710987.6, 4 pages.
European Search Report dated Jun. 5, 2014 in European App. No. 11710987.6, 4 pages.
European Search Report dated Oct. 31, 2013 in European App. No. 11710987.6, 3 pages.
Exam Report dated Sep. 15, 2016 in European Application No. 11710987.6, 3 pages.
Examination Report dated Mar. 2, 2017 in Australian Application No. 2015206267, 4 pages.
Final Office Action dated Aug. 30, 2016 in U.S. Appl. No. 14/667,441, 21 pages.
Final Office Action dated Oct. 20, 2016 in U.S. Appl. No. 13/488,326, 13 pages.
Kestle, J., et al., Long-term follow-up data from the Shunt Design Trial. Pediatr Neurosurg, 2000. 33(5): p. 230-236.
Kestle, J., R. Milner, and J. Drake, The shunt design trial: variation in surgical experience did not influence shunt survival. Pediatr Neurosurg, 1999. 30(6): p. 283-7.
Kestle, J.R., et al., Lack of benefit of endoscopic ventriculoperitoneal shunt insertion: a multicenter randomized trial. J Neurosurg, 2003. 98(2): p. 284-90.
Marmarou, Anthony, et al., Diagnosis and management of idiopathic normal-pressure hydrocephalus: a prospective study in 151 patients. Journal of Neurosurgery, Jun. 2005, vol. 102, pp. 987-997.
National Center for Health Statistics. Birth Data. National Vital Statistics System. [Online] [Cited: Aug. 26, 2010.] http://www.cdc.gov/nchs/births.htm.
National Institutes of Health. Hydrocephalus Fact Sheet. National Institute of Neurological Disorders and Stroke. [Online] Jul. 10, 2010. [Cited: Aug. 2, 2010.] http://www.ninds.nih.gov/disorders/hydrocephalus/detail_hydrocephalus.htm.
Office Action dated Aug. 23, 2016 in China Application No. 201180022356.X.
Patwardhan, Ravish V. and Nanda, Anil, Implanted Ventricular Shunts in the United States: The Billion-Dollar-A-Year Cost of Hydrocephalus Treatment. Neurosurgery, Jan. 2005, vol. 56, pp. 139-145.
Persson, Eva-Karin, et al., Hydrocephalus in children born in 1999-2002: epidemiology, outcome and ophthalmological findings. Childs Nervous System, 2007, vol. 23, pp. 1111-1118.
Rekate, Harold L., Hydrocephalus in Adults. Apr. 2007, Neurosurgical Focus, vol. 22, p. (Introduction).
Seshadri, S., et al., Lifetime risk of dementia and Alzheimer's Disease. American Academy of Neurology, 1997, vol. 49, pp. 1498-1504.
Sgouros, Spyros. Spina Bifida Family Support. [Online] [Cited: Aug. 13, 2010.] http://www.spinabifidasupport.com/defhydrocephalus.htm.
Simon, T.D., et al., Infection rates following initial cerebrospinal fluid shunt placement across pediatric hospitals in the United States. Clinical article. J Neurosurg Pediatr, 2009.4(2): p. 156-65.
Simon, Tamara D., et al., Hospital care for children with hydrocephalus in the Unites States: utilization, charges, comorbidities, and deaths. Journal of Neurosurgery: Pediatrics, Feb. 2008, vol. 1, pp. 131-137.
Williams, M.A., et al., Priorities for hydrocephalus research: report from a National Institutes of Health-sponsored workshop. J Neurosurg, 2007. 107(5 Suppl): p. 345-57.
Williams, Michael A., et al., Influence of shunt surgery on healthcare expenditures of elderly fee-for-service Medicare beneficiaries with hydrocephalus. Journal of Neurosurgery, Jul. 2007, vol. 107, pp. 21-28.
Akbar, M. et al., Adjustable cerebrospinal fluid shunt valves in 3.0-Tesla MRI: A phantom study using explanted devices, RöFo: Fortschritte Auf Dem Gebiet Der Röntgenstrahlenl Und Der Bildgebenden Verfahren, 182(7):594-602, Jul. 2010.
Inoue, T. et al., Effect of 3-tesla magnetic resonance imaging on various pressure programmable shunt valves, Journal of Neurosurgery, 103(2 Suppl):163-5, Aug. 2005.
Lollis, SS et al., Programmable CSF shunt valves: radiographic identification and interpretation, American Journal of Neuroradiology, 31(7):1343-6, Aug. 2010.
Zhong, J. et al., Advances in ICP monitoring techniques, Neurological Research, 25(4):339-50, Jun. 2003.
Non-Final Office Action dated Apr. 6, 2017 in U.S. Appl. No. 14/973,548, 61 pages.
Examination Report dated Jun. 15, 2017 in Canadian Patent Application No. 2936349, 3 pages.
Examination Report dated May 3, 2017 in Canadian Patent Application No. 2793675, 3 pages.
European Search Report dated May 4, 2016 in European App No. 11710987.6, 5 pages.
Exam Report in European Patent Application No. 11710987.6, dated Sep. 14, 2017, 4 pages.
Final Office Action dated Sep. 1, 2017 in U.S. Appl. No. 14/667,441, of Browd, S., et al., filed Mar. 24, 2015.
Non-Final Office Action dated Apr. 5, 2016 in U.S. Appl. No. 13/488,326, 22 pages.
Examination Report dated Jan. 15, 2018 in Canadian Patent Application No. 2,793,672, 3 pages.
Extended European Search Report dated Feb. 8, 2018 in European Patent Application No. 15737401.8, 6 pages.
European Examination Report dated Apr. 20, 2018 in European Patent Application No. 11710987.6, 4 pages.
Non-Final Office Action dated May 17, 2018 in U.S. Appl. No. 14/667,441, for Browd, S. et al., filed Mar. 24, 2015.
Final Office Action dated Nov. 30, 2017 in U.S. Appl. No. 13/488,326, of Browd et al., filed Jun. 4, 2012.
Exam Report in European Patent Application No. 11710987.6, dated Apr. 20, 2018, 4 pages.
Examination Report dated Feb. 27, 2018 in Canadian Patent Application No. 2,936,349, 3 pages.
International Search Report and Written Opinion dated Jul. 7, 2015 in International Patent Application No. PCT/US2015/024762, filed Apr. 7, 2015. 9 pages.
Non-Final Office Action dated Nov. 30, 2018 in U.S. Appl. No. 15/128,218 for Browd et al., filed Sep. 22, 2016, 13 pages.
Notice of Allowance dated Nov. 5, 2018 in U.S. Appl. No. 14/667,441 for Browd et al., filed Mar. 24, 2015.

(56) References Cited

OTHER PUBLICATIONS

Extended European Search Report dated Apr. 12, 2019 in European Patent Application No. 19153244.9, 11 pages.
Final Office Action dated Jun. 24, 2019 in U.S. Appl. No. 15/128,218 for Browd et al., filed Sep. 22, 2016, 17 pages.

* cited by examiner

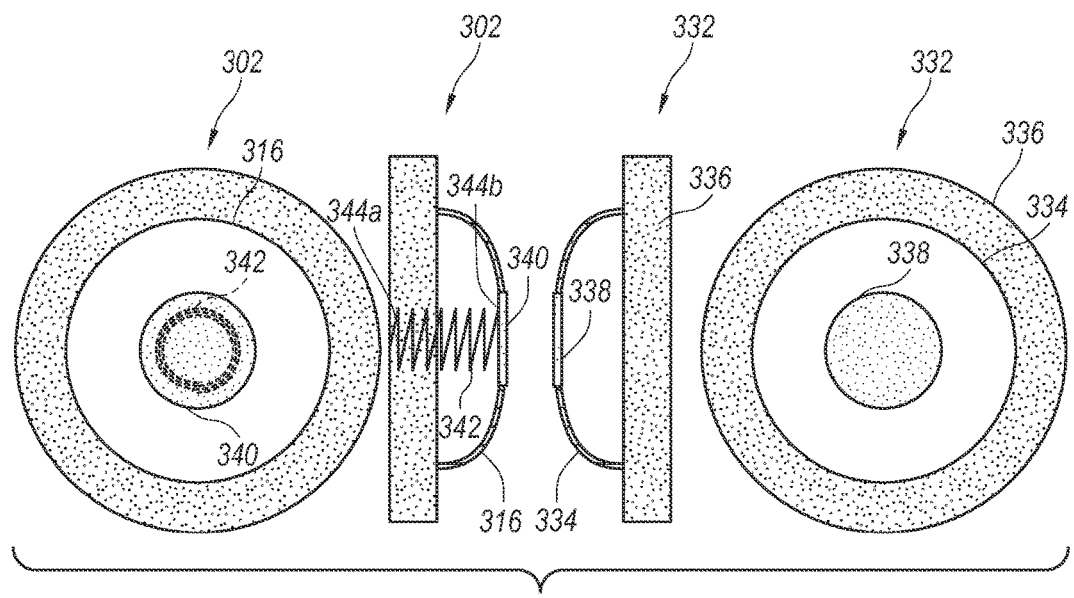
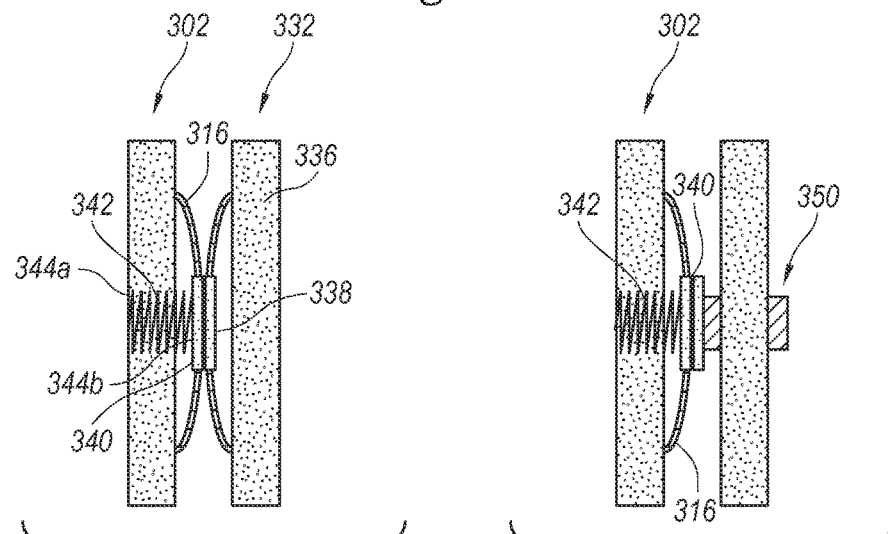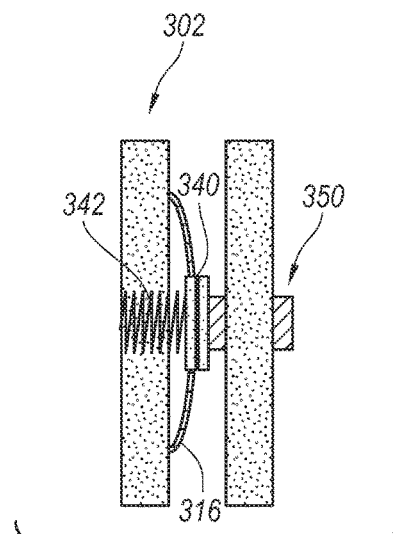
Fig. 3A
Fig. 3B   Fig. 3C ed generally to draining excess body fluids. In particular, several embodiments are directed toward pressure reference assemblies for body fluid drainage systems and associated methods.

PRESSURE REFERENCE ASSEMBLIES FOR BODY FLUID DRAINAGE SYSTEMS AND ASSOCIATED METHODS

CROSS-REFERENCE TO RELATED APPLICATION(S)

This application claims the benefit of U.S. Provisional Patent Application No. 61/928,286, filed Jan. 16, 2014, which is incorporated herein by reference in its entirety.

TECHNICAL FIELD

The present technology relates generally to draining excess body fluids. In particular, several embodiments are directed toward pressure reference assemblies for body fluid drainage systems and associated methods.

BACKGROUND

A variety of medical conditions cause a collection of excess body fluids within the human body. Hydrocephalus, for example, is an accumulation of excess cerebrospinal fluid ("CSF") in the ventricles of the brain that increases intracranial pressure ("ICP"). This condition can be caused by the inability to reabsorb CSF, impaired CSF flow, or excessive production of CSF. Acute accumulations of excess CSF can also occur from brain trauma, brain hemorrhaging, strokes, brain tumors, spinal fluid leaks, meningitis, and brain abscesses. When left untreated, hydrocephalus and other excess accumulations of CSF can progressively enlarge the ventricles of the brain, which increases ICP. When left untreated, high ICP results in convulsions, mental disabilities, and eventually death.

Treatment for hydrocephalus generally requires the installation of a CSF shunt that drains CSF from the brain to an alternate location that can collect the excess CSF or reabsorb it into the body. A ventriculoperitoneal shunt ("VPS"), for example, includes a subcutaneously installed catheter inserted in the lateral ventricle (i.e., a site of excess CSF) and in fluid communication with the peritoneal cavity to facilitate reabsorbtion of the excess CSF into the body. A mechanical valve, generally implanted flush with the skull, can regulate CSF flow through the catheter.

Similar to hydrocephalus, acute accumulations of CSF are treated by shunting excess CSF to an alternate location. For example, temporary CSF diversion generally includes the installation of an external ventricular drain ("EVD") that funnels CSF from the lateral ventricle to an external drainage chamber, thereby reducing the intracranial CSF volume and lowering ICP. Alternatively, temporary CSF diversion can include placing a lumbar drain ("LD") at the base of the spine, and draining CSF from the lumbar region to an external drainage chamber. Despite having different insertion points, EVDs and LDs use the similar components to control drainage.

In general, temporary and more permanent CSF diversion devices (e.g., VPSs) include similar features, and are therefore subject to many of the same technical challenges and complications. For example, it is important to accurately measure a patient's ICP to ensure that the flow rate through the shunt provides the necessary pressure relief to the brain. In addition, accurate ICP measurements are helpful in determining whether the CSF diversion device is functioning properly. The inlet of the catheter, for example, can incur in-growth of intraventricular tissue. Valves can fail due to debris build-up (e.g., blood, protein) within the valve, and the outlet of the catheter can fail by fracturing, becoming obstructed, or tethering within scar tissue. Moreover, infection can be a significant risk factor both during and after implantation of a CSF shunt. When an infection occurs, the entire CSF shunt must be removed, and the patient must generally undergo 10-14 days of IV antibiotics and re-internalization of a new CSF shunt. These mechanical failures, infections, and other complications cause a majority of implanted CSF shunts to fail within two years and nearly all shunts fail within ten years. Due to this unreliability and the necessity to locally monitor and adjust ICPs, conventional CSF shunts require frequent monitoring and intervention by medical professionals.

BRIEF DESCRIPTION OF THE DRAWINGS

FIG. 3A includes a front view and a side view of a drainage catheter and a pressure sensor of a body fluid drainage system configured in accordance with an embodiment of the present technology.

FIG. 3B is a side view of the drainage catheter and the pressure sensor of FIG. 3A placed in contact with each other in accordance with an embodiment of the present technology.

FIG. 3C is a side view of a drainage catheter and a force sensor configured in accordance with another embodiment of the present technology.

DETAILED DESCRIPTION

The present technology is directed to devices, systems, and methods for draining excess body fluids and pressure reference assemblies configured to determine pressure at the site of excess body fluid. In one embodiment, for example, a body fluid drainage system can be installed between a site of excess body fluid in a patient, such as within a patient's head, and a second location (e.g., an external receptacle, an internal cavity) that can collect and/or reabsorb the excess body fluid. The body fluid drainage system also includes a pressure reference assembly that determines the pressure at the site of excess body fluid without measuring the pressure directly at the site of excess fluid. Certain specific details are set forth in the following description and in FIGS. 1A-11 to provide a thorough understanding of various embodiments of the technology. For example, several embodiments of body fluid drainage systems that shunt cerebrospinal fluid ("CSF") are described in detail below. The present technology, however, may be used to drain a variety of excess body fluids, such as peritoneal fluid, blood, water, and/or other body fluids. Additionally, the term "catheter" is used broadly throughout the application to refer to any suitable tubing or structure that includes a lumen through which body fluids can flow. Other details describing well-known structures and systems often associated with CSF and other body fluid drainage systems, shunts, biomedical diagnostics, etc. have not been set forth in the following disclosure to avoid unnecessarily obscuring the description of the various embodiments of the technology. A person of ordinary skill in the art, therefore, will accordingly understand that the technology may have other embodiments with additional elements, or the technology may have other embodiments without several of the features shown and described below with reference to FIGS. 1A-11.

Figure 1A:
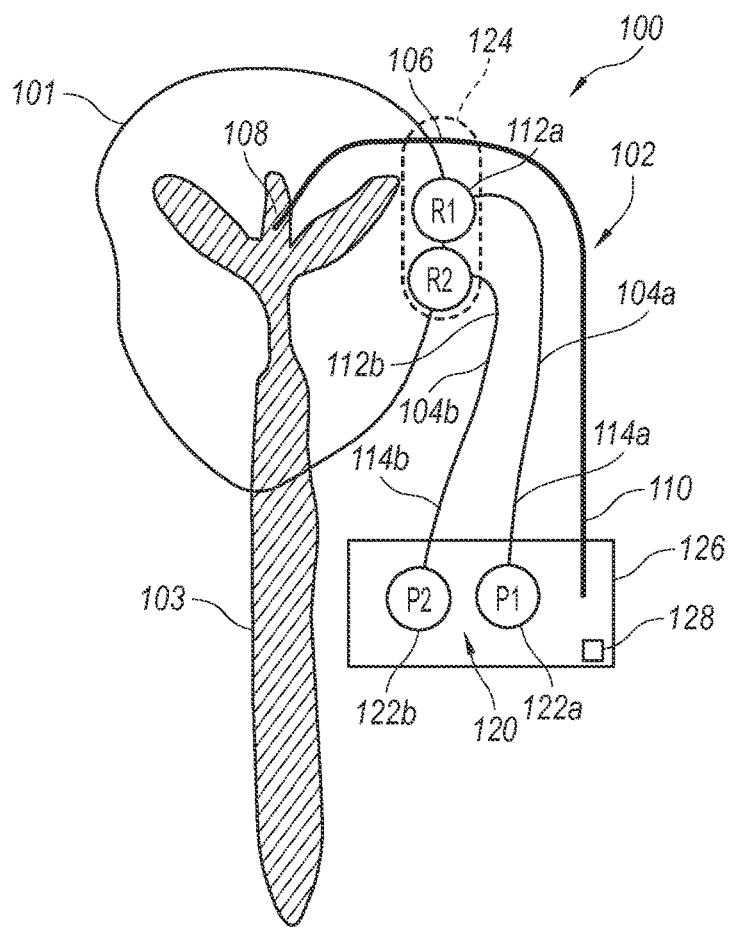
FIG. 1A is a partially schematic illustration of a patient with a body fluid drainage system configured in accordance with an embodiment of the present technology.
Figure 1B:
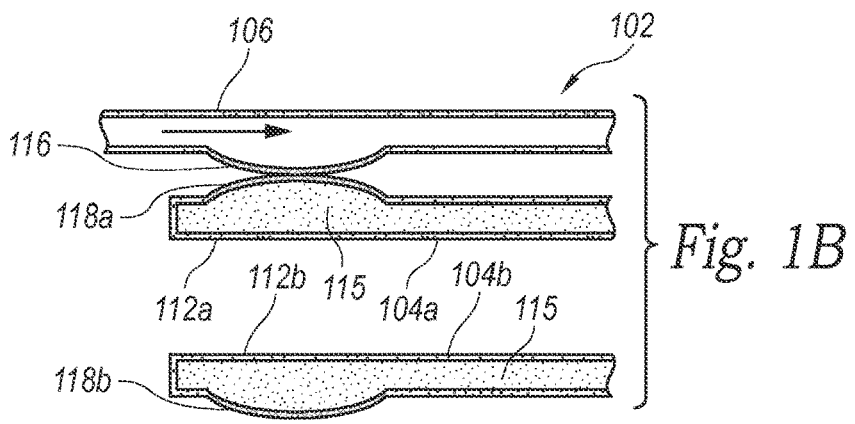
FIG. 1B is an enlarged cross-sectional view of a proximal portion of a drainage catheter and pressure reference lines of the body fluid drainage system of FIG. 1A.

Selected Embodiments of Body Fluid Drainage Systems with Pressure Reference Assemblies FIG. 1A is a partially schematic illustration of a patient 101 with a body fluid drainage system 100 ("drainage system 100") configured in accordance with an embodiment of the present technology, and FIG. 1B is an enlarged cross-sectional view of a proximal portion of the drainage system 100 of FIG. 1A. The drainage system 100 includes a drainage catheter 102, a first reference line 104a, and a second reference line 104b (referred to collectively as "reference lines 104"). The drainage catheter 102 has a proximal portion 106 with an inlet 108 in fluid communication with a site of excess body fluid within the patient 101 and a distal portion 110 spaced apart from the proximal portion and configured to dispense the excess fluid in an external receptacle or internal body cavity where the fluid can be collected and/or reabsorbed. In the embodiment illustrated in FIG. 1A, for example, the drainage system 100 is configured to shunt CSF away from the patient's brain, and therefore the inlet 108 of the drainage catheter 102 is positioned in the patient's lateral ventricle in fluid communication with the CSF system 103. In other embodiments, the drainage system 100 can be used to drain excess fluid from other portions of the body.

The reference lines 104 each comprise a tube or catheter that is at least substantially filled with a reference fluid 115. The first reference line 104a has a first portion 112a and a second portion 114a opposite the first portion 112a, and the second reference line 104b has a first portion 112b opposite a second portion 114b. As shown in FIG. 1A, the first portions 112a, 112b (collectively referred to as "first portions 112") of the first and second reference lines 104a and 104b are positioned proximate to each other (e.g., substantially co-located) at a first location or reference point near the site of excess body fluid and the inlet 108 of the drainage catheter 102, and the second portions 114a, 114b (collectively referred to as "second portions 114") of the first and second reference lines 104a and 104b are at a second location spaced away from the site of excess body fluid. In the illustrated embodiment, for example, the proximal ends of the reference lines 104 are positioned near the patient's head (e.g., at the ear) close to the lateral ventricle. The second portions 114 of the reference lines 104 can be coupled to a pressure sensor assembly 120 that is configured to measure pressure at the second portions 114 of the first and second reference lines 104a and 104b. In the embodiment illustrated in FIG. 1A, the pressure sensor assembly 120 includes a first pressure sensor 122a at the second location in pressure communication with the second portion 114a of the first reference line 104a, and a second pressure sensor 122b at the second location in pressure communication with the second portion 114b of the second reference line 104b. In other embodiments, the pressure sensor assembly 120 can include a single pressure sensor configured to measure the differential pressure between the first and second reference lines 104a and 104b at the second location and/or other types of sensors that can derive pressure within the reference lines 104. In other embodiments, the reference lines 104 can be operably coupled to a sensor assembly 120 that is configured to take different or addition types of measurements from the reference lines 104. For example, the sensor assembly 120 can be configured to take force measurements that can be used to determine pressure at the proximal portion 106 of the drainage catheter 102.

As shown in FIG. 1B, the proximal portion 106 of the drainage catheter 102 has a flexible interface member 116, the first portion 112a of the first reference line 104a has a first flexible region 118a in pressure communication (e.g., physical contact) with the flexible interface member 116, and the first portion 112b of the second reference line 104b has a second flexible region 118b in pressure communication with the surrounding atmosphere of the flexible interface member 116 and the first and second flexible regions 118a and 118b (referred to collectively as "the flexible regions 118"). For example, the second flexible region 118b can be exposed to the surrounding air (e.g., atmospheric pressure). In operation, the flexible interface member 116 of the drainage catheter 102 expands or inflates as fluid pressure within the drainage catheter 102 increases (e.g., representing an increase in ICP), and retracts or deflates as fluid pressure within the drainage catheter 102 decreases (e.g., representing a decrease in ICP). The fluctuations of the flexible interface member 116 (e.g., representative of fluctuations in ICP) are communicated to the first flexible region 118a. That is, when the pressure within the flexible interface member 116 increases, the flexible interface member 116 applies more pressure against the first flexible region 118a, and vice versa. Accordingly, the pressure measured by the first pressure sensor 122a at the second portion 108a of the first reference line 104a represents the pressure within the drainage catheter 102 at the first location (e.g., near the site of excess fluid) plus the pressure head of the reference fluid 115 within the first reference line 104a. Because the second flexible region 118b is exposed to the atmosphere at the first location, the pressure measured by the second pressure sensor 122b at the second portion 108b of the second reference line 104b corresponds to the pressure head within the second reference line 104b. This pressure measurement is at least substantially equal to the pressure head in the first reference line 104a because the two reference lines 104 contain the same reference fluid 115, have the same length, and the flexible regions 118 and the pressure sensors 122 of each reference line 104 are near the same location. Therefore, the pressure of the drainage catheter 102 at the first location is equivalent to the pressure measured by the first pressure sensor 122a less the pressure measured by the second pressure sensor 122b. When the first location is located near the lateral ventricles (e.g., at the side of the patient's head), this pressure is approximately equal to the ICP. If different reference fluids or reference line lengths are used, the drainage system 100 may include algorithms that correct for such differences to determine the pressure head in the first reference line 104a.

As further shown in FIG. 1B, the proximal ends of the reference lines 104 are sealed from the environment and the distal ends can be similarly sealed to enclose the reference fluid 115 within the reference lines 104. The reference lines 104 can be made of polyurethane tubing and/or other suitable materials for sealing the reference fluid 115 therein. In the embodiment illustrated in FIG. 1B, the flexible region 118 of each reference line 104 is spaced along the length of the corresponding reference line 104 and positioned on a side of the reference line 104. In other embodiments, one or both of the flexible regions 118 can extend from the proximal-most end of each reference line 104. The flexible regions 118 of the reference lines 104 can be flexible membranes or diaphragms made from substantially flexible materials that are sensitive to changes in pressure and the application of small forces thereon, such as the forces applied by the opposing flexible interface member 116 when pressure changes within the drainage catheter 102. For example, the flexible regions 118 can be made from ether- or ester-based materials. In other embodiments, the flexible regions 118 can be made from other suitable flexible materials. The flexible regions 118 can be attached to the reference lines 104 via molding, adhesives, and/or other suitable connection techniques, or the flexible regions 118 can be integrally formed with the reference lines 104. For illustrative purposes, the flexible members 118 are shown protruding outwardly from the sides of the reference lines 104. However, under normal conditions when no external pressures are applied to the flexible members 118, the flexible members 118 can be in a relaxed or flaccid state such that the material of the flexible members 118 is not stretched or placed under tension. Accordingly, the flexible members 118 may appear substantially in line with the sidewall of the reference lines 104. Then, when a force acts on one of the flexible members 118, it can move inwardly or outwardly depending on the force applied. In other embodiments, the flexible members 118 may be configured such that the normal, relaxed state of the material causes the flexible members 118 to protrude outwardly or inwardly. The drainage catheter 102 and the flexible interface member 116 can be made from similar materials as the reference lines 104 and the flexible regions 118, respectively.

The reference fluid 115 can be configured to completely fill the reference lines 104 such that the flexible regions 118 are in a relaxed state such that they can move (e.g., stretch) in either direction in response to the movement of an opposing flexible interface member 116. The reference fluid 115 can include silicone oil, mineral oil, propylene glycol, and/or other fluids with high vapor pressures that limit the amount of evaporation of the fluid during storage and use of the reference lines 104. In other embodiments, the reference lines 104 can be filled with other types of fluids, such a saline or water. In certain embodiments, the same reference fluid 115 is used in both reference lines 104 such that the pressure measurements taken by the two pressure sensors 122 or a differential pressure sensor can be directly subtracted from each other to determine the pressure of the drainage catheter 102 at the reference point. In other embodiments, different reference fluids 115 may be used in the reference lines 104 and the pressure sensor assembly 120 can be configured to correct for the differences in fluid density.

In various embodiments, the flexible interface member 116 of the drainage catheter 102 and the flexible regions 118 of the reference lines can be housed at least partially within a cartridge 124 (FIG. 1A; shown in broken lines). The cartridge 124 may be a durable case or container that provides protection for the interface member 116, the flexible regions 118, and/or any other system components (e.g., electronics) stored therein, and further include attachment features that position the interface member 116 and the flexible regions 118 appropriately with respect to each other. For example, the cartridge 124 can include protrusions or grooves that receive the reference lines 104 and the drainage catheter 102, position the two flexible regions 118 such that the two reference lines 104 experience the same pressure head, and position the flexible interface member 116 to be in pressure communication with one of the flexible regions 118. The cartridge 124 is further configured to be positioned at a reference location on the patient 101 close to the drainage site. For example, the cartridge 124 can be positioned above the patient's ear when the drainage system 100 is configured for draining CSF from the brain. In other embodiments, the cartridge 124 can be positioned proximate to other drainage sites, such as in the patient's lumbar region when the drainage system 100 is used as a lumbar drain. In certain embodiments, the first portions 112 of the two reference lines 104 can be pre-packaged within the cartridge 124 such that the flexible regions 118 are affixed in a desired position (e.g., next to each other, at the same elevation, substantially co-located, etc.). The proximal portion 106 of the drainage catheter 102 can then be positioned within the prepackaged cartridge 124 such that the flexible interface member 116 is in pressure communication (e.g., physically in contact) with one of the flexible regions 118. For example, the cartridge 124 may include attachment features that appropriately position the flexible interface member 116 with respect to one of the flexible regions 118. This embodiment facilitates use of the reference lines 104 and the associated assembly (e.g., the cartridge 124 and the pressure sensor assembly 120) with previously-implanted drainage catheters. In addition, the prepackaged configuration provides a multi-use reference line assembly (e.g., the reference lines 104 and the pressure sensor assembly 120) that can be used on multiple occasions and/or with different patients. In other embodiments, the cartridge 124 can be preassembled with the drainage catheter 102 and the reference lines 104 such that the flexible interface member 116 and the flexible regions 118 are affixed in the desired positions with the interface member 116 contacting or attached to the first flexible region 118a. In further embodiments, the proximal elements of the drainage system 100 can be assembled within the cartridge 124 during or after the drain implantation procedure. In still further embodiments, the cartridge 124 can be omitted, and the proximal elements of the drainage system 100 can be positioned appropriately with respect to each other and with respect to the patient 101 using other suitable means.

In various embodiments, the reference line assembly (e.g., the two reference lines 104 and related components) can be configured to measure negative pressures within the drainage catheter 102. When the flexible interface member 116 is subject to negative pressures, it may retract and, as a result, may come out of contact with the opposing first flexible region 118a of the first reference line 104. This loss of contact prevents the first flexible member 118a from translating the movement of the flexible interface member 116 to pressure measurements. Accordingly, the reference line assembly can include features that maintain contact between the first flexible region 118a and the flexible interface member 116, regardless of the direction of movement of the flexible interface member 116. For example, when the drainage catheter 102 and the first reference line 104a are preassembled (e.g., within the cartridge 124), the flexible interface member 116 and the first flexible region 118a can be permanently bonded together. Various additional features for maintaining at least semi-permanent contact between the flexible interface member 116 and an opposing membrane (e.g., the first flexible region 118a) under negative pressures are described below with reference to FIGS. 3A-7, and can be used with the drainage system 100 to at least temporarily attach the flexible interface member 116 to the first flexible region 118a. In further embodiments, the drainage catheter 102 and the first reference line 104a can be attached (e.g., bonded) together at least in the area around the flexible interface member 116 and a single membrane can be used to detect pressure changes in the drainage catheter 102. In this embodiment, the flexible interface member 116 or the first flexible region 118a is omitted, leaving an opening in one of the drainage catheter 102 or the first reference line 104a that is configured to receive the remaining of the first flexible region 118a or the flexible interface member 116. When the catheter 102 and the first reference line 104a are attached together, the remaining membrane (i.e., the flexible interface member 116 or the first flexible region 118a) can be positioned between the reference fluid 115 and the fluid in the drainage catheter 102 and act directly on the reference fluid 115 to reflect changes in the pressure of the drainage catheter 102.

As further shown in FIG. 1A, the drainage system 100 can also include a housing 126 that carries the pressure sensor assembly 120 and the second portions 114 of the reference lines 104. Similar to the cartridge 124, the housing 126 can be configured to secure the reference lines 104, the pressure sensor assembly 120, and optionally the drainage catheter 102, and position these elements appropriately with respect to each other. For example, the housing 126 can include grooves or protrusions that position the first and second pressure sensors 122a and 122b at about the same elevation such that they measure the same amount of pressure head in the corresponding reference lines 104. In the illustrated embodiment, the drainage catheter 102 terminates at the same point as the pressure sensors 122, but in other embodiments the drainage catheter 102 can extend to a different location and/or beyond the housing 126 to an internal or external receptacle (not shown) that can collect the drained body fluid. The housing 126 can also carry a processor or processing device 128 (shown schematically; e.g., a central processing unit (CPU)) and/or additional elements of the drainage system 100, such as a receptacle (not shown) into which the excess body fluid from the catheter 102 can drain.

The processing device 128 can be operably coupled to the pressure sensor assembly 120 and/or other features of the drainage system 100 (e.g., valves). The processing device 128 can include or be part of a device that includes a hardware controller that interprets the signals received from input devices (e.g., the pressure sensors 122, other sensors, user input devices, etc.) and communicates the information to the processing device 128 using a communication protocol. The processing device 128 may be a single processing unit or multiple processing units in a device or distributed across multiple devices. The processing device 128 may communicate with the hardware controller for devices, such as for a display that displays graphics and/or text (e.g., LCD display screens). The processing device 128 can also be in communication with a memory (e.g., within the housing 126) that includes one or more hardware devices for volatile and non-volatile storage, and may include both read-only and writable memory. For example, a memory may comprise random access memory (RAM), read-only memory (ROM), writable non-volatile memory, such as flash memory, hard drives, floppy disks, CDs, DVDs, magnetic storage devices, tape drives, device buffers, and so forth. A memory is not a propagating electrical signal divorced from underlying hardware, and is thus non-transitory. In certain embodiments, the processing device 128 can also be coupled to a communication device capable of communicating wirelessly or wire-based with a network node. The communication device may communicate with another device or a server through a network using, for example, TCP/IP protocols.

The processing device 128 can execute automated control algorithms to initiate, terminate, and/or adjust operation of one or more features of the pressure sensor assembly 120 and/or receive control instructions from a user. The processing device 128 can further be configured to provide feedback to a user based on the data detected by the pressure sensor assembly 120 via an evaluation/feedback algorithm. For example, the processing device 128 can be configured to provide clinicians, patients, and/or other users with a patient's pressure level at a site of excess body fluid (e.g., ICP), indicators of when a threshold pressure level is exceeded, and/or other pressure-related information based on the information received from the pressure sensors 122. This information can be provided to the users via a display (e.g., a monitor on a computer, tablet computer, or smart phone; not shown) communicatively coupled to the processing device 128.

In operation, the pressure in the drainage catheter 102 near a site of excess body fluid (e.g., the brain) can be determined using measurements taken from the separate reference lines 104, and do so using pressure measurements obtained at a location spaced apart from the site of excess body fluid. For example, when the drainage system 100 is configured to drain CSF from the patient's brain, ICP can be determined by taking pressure measurements with the pressure sensor assembly 120 at a location spaced distant from and, optionally, movable with respect to the patient's head. Thus, the pressure sensor assembly 120 can be spaced distant from the patient's head. This allows the pressure readings provided by the pressure sensor assembly 120 and/or the ICP determined via the pressure sensor assembly 120 or processing device 128 to be displayed to a user at a convenient location. For example, rather than a clinician having to look at a pressure sensor reading on a patient's head to determine ICP, the drainage system 100 allows the pressure sensor assembly 120 and associated display to be positioned at a location that is convenient and/or easily accessible for the clinician (e.g., at chest level when the clinician is in a standing location, at table level, spaced apart from the patient 101). The clinician can use the two pressure measurements to determine the desired pressure at the excess fluid site, or the processing device 128 can automatically calculate this information for the clinician. The mobility of the pressure sensor assembly 120 and associated devices (e.g., the processing device 128, displays, etc.) is also more comfortable for a patient 101 because the pressure sensor need not be attached to his or her head or body. Accordingly, the drainage system 100 allows ICP and other pressure measurements to be determined without having a pressure sensor directly at the patient's head or other site of excess body fluid. In addition, because the drainage system 100 does not take pressure measurements directly from the drainage catheter 102 itself, the pressure measurements taken by the pressure sensor assembly 120 are not subject to losses that may occur due to fluid flow through the drainage catheter 102. Accordingly, the drainage system 100 is expected to increase the accuracy of pressure measurements taken at a location spaced apart from the site of excess body fluid.

Figure 2A:
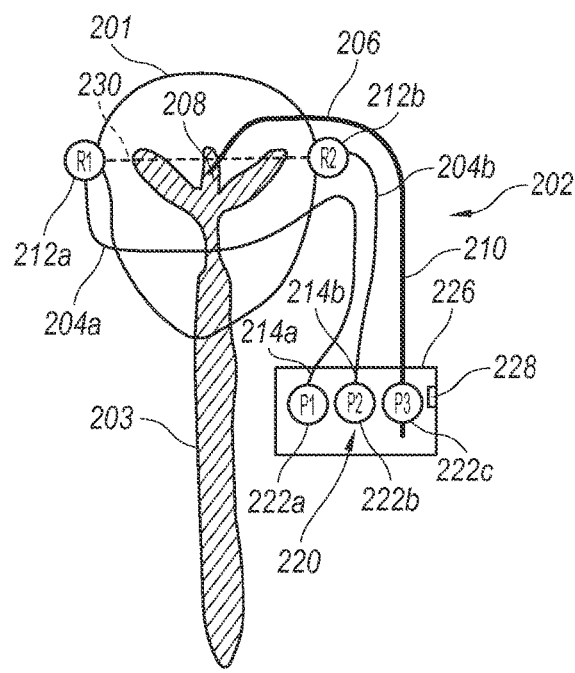
FIG. 2A is a partially schematic illustration of a patient with a body fluid drainage system configured in accordance with another embodiment of the present technology.
Figure 2B:
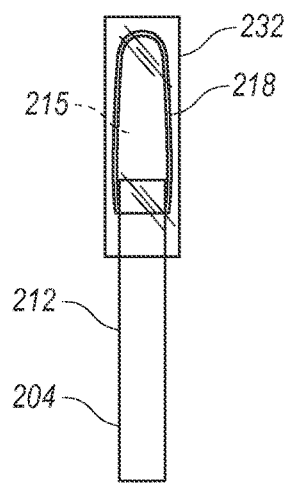
FIG. 2B is an enlarged view of a proximal end portion of a reference line of the body fluid drainage system of FIG. 2A configured in accordance with an embodiment of the present technology.

FIG. 2A is a partially schematic illustration of a patient 201 with a body fluid drainage system 200 ("drainage system 200") configured in accordance with another embodiment of the present technology, and FIG. 2B is an enlarged view of a proximal end portion of a reference line 204 of the drainage system 200. The drainage system 200 can include several features generally similar in structure and function to the features of the drainage system 100 described above with reference to FIGS. 1A and 1B. As shown in FIG. 2A, for example, the drainage system 200 includes a drainage catheter 202, a first reference line 204*a*, and a second reference line 204*b* (collectively referred to as "reference lines 204"). The drainage catheter 202 has a proximal portion 206 with an inlet 208 in fluid communication with a site of excess body fluid within the patient 201 and a distal portion 210 opposite the proximal portion 206. The first and second reference lines 204*a* and 204*b* are filled with a reference fluid 215 (FIG. 2B), and each have a proximal or first end portion 212*a*, 212*b* (referred to collectively as "first end portions 212") and a distal or second end portion 214*a*, 214*b* (referred to collectively as "second end portions 214") opposite the first end portion 212*a*, 212*b*. The proximal end portions 212 include a flexible region 218 (FIG. 2B) that is in pressure communication with the surrounding air (i.e., exposed to atmospheric pressure). As shown in FIG. 2B, in certain embodiments the flexible region 218 is a pliable membrane that extends from the proximal end of the reference line 204 to form a balloon-like structure filled with the reference fluid 215 and exposed to the atmosphere. An end cap 232 or other type of housing can be positioned around the flexible region 218 to prevent external objects from applying pressure to the flexible region 218 such that the flexible region 218 is only subject to changes in the surrounding atmospheric pressure. In other embodiments, the flexible regions 218 of one or both of the reference lines 204 can protrude outwardly from a sidewall of the first end portion 212 of the reference line 204 (e.g., similar to the flexible regions 118 described with reference to FIG. 1B).

As shown in FIG. 2A, the drainage system 200 can further include a pressure sensor assembly 220 positioned at the distal end portions 214 of the reference lines 204 and operably coupled to the distal portion 210 of the drainage catheter 202 and the second end portions 214 of the first and second reference lines 204*a* and 204*b*. The pressure sensor assembly 220 can be configured to measure pressure within the drainage catheter 202 at the distal portion 210, and the pressure within the reference lines 204 at the second end portions 214. In the illustrated embodiment, for example, the pressure sensor assembly 220 includes a first pressure sensor 222*a* at the second end portion 216*a* of the first reference line 204*a*, a second pressure sensor 222*b* at the second end portion 216*b* of the second reference line 204*b*, and a third pressure sensor 222*c* at the distal portion 210 of the drainage catheter 202. In other embodiments, the pressure sensor assembly 220 can include less than three pressure sensors, more than three pressure sensors, and/or other types of sensors that can be used to determine the pressure within the distal portions of the drainage catheter 202 and the reference lines 204. As shown in the illustrated embodiment, the three pressure sensors 222*a*-222*c* can be positioned at the same location, at a position spaced apart from the site of excess body fluid. As described in further detail below, the measurements taken from the pressure sensor assembly 220 can be used to determine the pressure at the site of excess body fluid (i.e., the drainage site).

As further shown in FIG. 2A, the drainage system 200 can include a housing 226 that carries the pressure sensor assembly 220. The housing 226 can also carry other features associated with the drainage system 200, such as a processing device 228 and/or a display (not shown). Similar to the processing device 128 described above, the processing device 228 can include or be associated with a controller, and can be configured to run algorithms that control operation of the drainage system 200 and/or provide feedback to users regarding pressure measurements and/or the operation of the drainage system 200. This feedback can be provided to users on a display connected to the housing 226 and/or displays remote from the drainage system 200 and communicatively coupled thereto (e.g., via a wired or wireless connection).

During a system set-up procedure, a clinician can position the flexible regions 218 of the first end portions 212 of the first and second reference lines 204 at two points along an imaginary reference axis 230 (i.e., a straight line) that extends through the site of excess body fluid (i.e., the site at which the pressure measurement is desired). This site generally corresponds to the implantation location of the inlet 208 of the drainage catheter 202 and is also referred to herein as the "drainage site". The flexible region 218 of the first reference line 204*a* can be positioned at a first location along the reference axis 230 to one side of the drainage site, and the flexible region 218 of the second reference line 204*b* can be positioned at a second location along the reference axis 230 on the other side of the drainage site. Accordingly, the proximal end portions 212 of the first and second reference lines 204*a* and 204*b* are positioned on either side of the drainage site along the reference axis 230.

Figure 2C:
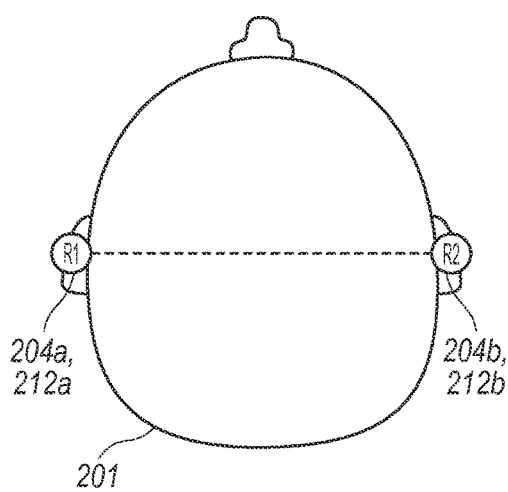
FIGS. 2C and 2D are top and side views of proximal portions of the body fluid drainage system of FIG. 2A positioned with respect to a patient's head.
Figure 2D:
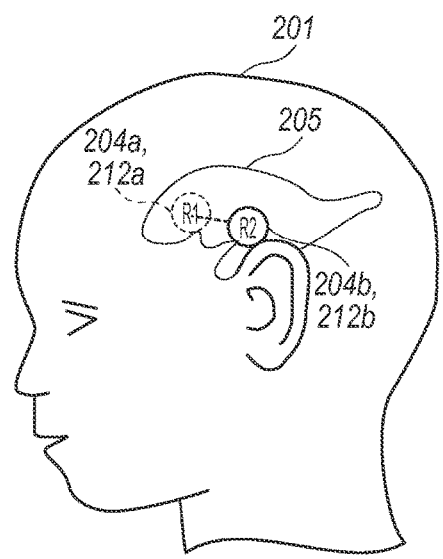

For example, when the drainage system 200 is intended to drain CSF from a patient's brain, the reference axis 230 is a straight line that extends through the lateral ventricles or the Foramen of Monroe (i.e., the center of the head). As shown in the embodiment illustrated in FIG. 2A, the first end portions 212 of the reference lines 204 can be placed along the reference axis 230 on either side of the patient's head, approximately equidistant from the drainage site. FIGS. 2C and 2D are top and perspective side views further illustrating the positioning of the first end portions 212 with respect to a patient's head and the lateral ventricles 205 (FIG. 2D). In this embodiment, the ICP (i.e., the desired pressure measurement) is equivalent to the pressure in the drainage catheter 202 measured by the third pressure sensor 222*c* less the pressure head between the inlet 108 of the drainage catheter 202 and the third pressure sensor 222c (i.e., the distance between the Foramen of Monroe and the location at which the pressure measurement is taken). The reference lines 204, with the flexible regions 218 (FIG. 2B) exposed to the atmosphere, can be used to determine the pressure head from the drainage site. More specifically, because the first end portions 212 of the two reference lines 204 are spaced approximately evenly apart from the Foramen of Monroe (i.e., the drainage site), the average of the two pressures measured by the first and second pressure sensors 222a and 222b is approximately equivalent to the pressure head (vertical distance) between the Foramen of Monroe and the location of the pressure sensors 222a-c. Therefore, the first and second reference lines 204a and 204b can be used to determine the pressure head from the actual drainage site (i.e., the lateral ventricles of the brain or other site at which the pressure measurement is desired) rather than at a position spaced laterally apart from the drainage site (e.g., over the patient's ear). Accordingly, the three pressure measurements taken from the three pressure sensors 222a-c can be used to determine the pressure at the Foramen of Monroe, which corresponds to the patient's ICP. More specifically, the ICP is equivalent to the pressure of the drainage catheter (P3) minus the average of measured pressures (P1 and P2) of the first and second reference lines 204a and 204b (i.e., ICP=P3−(P1+P2)/2). The calculation of drainage site pressure can be performed automatically via programs stored on the processing device 228 and/or manually using the pressure read outs provided by the pressure sensor assembly 220. The same type of calculations can be performed to determine the pressure at other sites of excess fluid around which the drainage system 200 is positioned. For example, when the drainage site is at the patient's abdomen, the reference axis 230 can extend through the drainage site, and the first end portions 212 of the two reference lines 204 can be positioned along the reference axis 230.

In the illustrated embodiment, the first end portions 212 of the reference lines 204 are about equidistant from the Foramen of Monroe (i.e., the drainage site). However, in other embodiments the first end portions 212 of the two reference lines 204 may be spaced different distances apart from the drainage site along the reference axis 230. In this embodiment, the pressure measurements of the first and second reference lines 204a and 204b can be weighted based on their position with respect to the drainage site. For example, the pressure measurement taken from the reference line 204 located closer to the drainage site would be weighted more heavily than the pressure measurement taken from the reference line that is spaced further from the drainage site, and the degree to which the pressure measurements are weighted can correspond to the relative closeness of the two reference lines from the drainage site. The weighted pressure measurements can then be used in conjunction with the measured pressure of the drainage catheter 202 to determine the pressure at the drainage site (e.g., ICP).

In use, the reference lines 204 are used with the pressure measured in the drainage catheter 202 to correct for the pressure head in the drainage catheter 202 when pressure is measured at a location spaced apart from the drainage site. The use of the two reference lines 204 placed along the reference axis 230 that passes through the drainage site allows for determination of the pressure head at a specific location (i.e., the drainage site) on the reference axis 230 between the proximal end portions 212 of the reference lines 204, instead of simply the pressure head within the reference lines 204. This allows the drainage system 200 to account for differences between the pressure head at the drainage site and the pressure head at a location spaced laterally apart from the drainage site, which may be caused by the orientation of the patient 201 (e.g., when the patient 201 is laying down rather than standing). Accordingly, the drainage system 200 can be used to determine the pressure at a drainage site (e.g., ICP) using sensors spaced apart from the drainage site, and does so with increased accuracy by determining the pressure head at the actual drainage site. For example, in certain embodiments the drainage system 200 can be used to determine the pressure at the drainage site (e.g., ICP) within 10-20 cm of water of the true pressure at the drainage site. In other embodiments, the drainage system 200 can be used to determine drainage site pressures with higher accuracy.

In other embodiments, the drainage system 200 can include more than two reference lines 204, each with a proximal end portion positioned along reference axis that pass through the drainage site and distal end portions attached to pressure sensors. The pressure head at the drainage site can be determined using the pressure measurements taken from each of the reference lines 204. For example, in certain embodiments the drainage system 200 includes three reference lines 204 placed on the patient's head. The three reference lines 204 can be used to determine the orientation of the patient's head and triangulate the pressure at any location within the brain.

In further embodiments, the drainage system 200 can be combined with the drainage system 100 of FIGS. 1A and 1B. For example, an additional reference line can be added that is in pressure contact with a flexible interface member on the proximal portion 206 of the drainage catheter 202 (e.g., as shown in FIG. 1B). In this embodiment, pressure measurements are taken from the additional reference line (e.g., a third reference line) rather than the drainage catheter 202 itself. These pressure measurements represent the pressure in the drainage catheter (e.g., ICP) plus the pressure head, and therefore can be used similarly to the pressure measurements taken directly from the drainage catheter. As discussed above, the pressure measurements taken from this additional reference line are not subject to losses associated with fluid flow through the drainage catheter 202 because the reference fluid within this additional reference line is substantially stagnant. Accordingly, this embodiment can increase the accuracy with which the pressure at the site of excess body fluid can be determined.

Selected Embodiments of Body Fluid Drainage Systems for Measuring Negative Pressures FIGS. 3A-8 illustrate various embodiments of body fluid drainage systems in which a flexible membrane or diaphragm of a drainage catheter is outwardly biased. As discussed above with respect to FIGS. 1A and 1B, the pressure in a drainage catheter can be measured across two membranes that are in contact. For example, the drainage catheter can include a flexible membrane that contacts (1) an opposing membrane of a reference line (e.g., the reference lines 104 described above) from which a pressure measurement can be taken via a pressure sensor along the reference line, (2) an opposing fluid-filled membrane of a pressure sensor, or (3) an opposing member of a force sensor (e.g., a load cell). This configuration isolates the measurements taken by the sensor from the fluid being measured (i.e., the fluid flowing through the drainage catheter). However, when the fluid pressure within the flexible membrane of the drainage catheter is less than the surrounding atmosphere (i.e., atmospheric pressure), the flexible membrane experiences a smaller pressure on the inside of the membrane than on the outside, and the membrane collapses or becomes retracted. This can result in the drainage catheter membrane from breaking contact with the sensing membrane or surface, and therefore prevents the sensing member (e.g., a pressure sensor with a fluid-filled diaphragm, a load cell, or a reference line with a pressure sensor attached thereto) from measuring the negative pressure. The embodiments described below with reference to FIGS. 3A-8 allow for the measurement of both positive and negative pressures via flexible membranes on drainage catheters. The embodiments described below may be used in conjunction with the drainage systems 100 and 200 described above with reference to FIGS. 1A-2D, as well as with other drainage catheter systems.

FIG. 3A includes a front view and a side view of a drainage catheter 302 and a pressure sensor 332 for a body fluid drainage system configured in accordance with an embodiment of the present technology, and FIG. 3B is a side view of the drainage catheter and the pressure sensor 332 of FIG. 3A placed in contact with each other. As shown in FIG. 3A, the drainage catheter 302 can include a flexible interface member 316, such as a diaphragm or flexible membrane, that protrudes outwardly from a wall of the drainage catheter 302 when filled with a fluid (e.g., excess body fluid being drained form the body). The drainage catheter 302 and the flexible interface member 316 can have a structure and function at least generally similar to the structure and function of the drainage catheters 102 and 202 and the flexible interface members 116 and 216 described above. The flexible interface member 316 can be positioned anywhere along the length of the drainage catheter 302, and can be used to determine the pressure at the drainage site. For example, as described above, the pressure detected at the flexible interface member 316 is equal to the pressure at the drainage site plus the pressure head between the drainage site and the flexible interface member 316. In embodiments including reference lines that measure pressure at a location spaced apart from the flexible interface member, the pressure head is between the drainage site and the location at which the pressure measurement is actually taken. Various features can be used to determine the pressure head (e.g., the reference lines 104 and 204 described above), and this information along with the pressure of the drainage line measured via the flexible interface member 316 can be used to derive the pressure at the drainage site (e.g., ICP).

As shown in FIGS. 3A and 3B, the pressure sensor 332 can include a fluid-filled diaphragm or membrane 334 that protrudes outwardly from a base portion 336 of the pressure sensor 332. The base portion 336 can house electronics and/or other features that are used to detect pressure via the membrane 334. The pressure sensor 332 can also include a contact member 338 on or along the membrane 334 against which the flexible interface member 316 of the drainage catheter 302 can be pressed (e.g., as shown in FIG. 3B). In various embodiments, the drainage catheter 302 can also include a contact member 340 that is configured to press against the opposing portion of the pressure sensor 332 and/or other sensor. The contact members 338 and 340 can be separate structures attached to the membrane 334 and flexible interface member 316, respectively, and may have different material properties than the underlying membranes 334, 316. For example, the contact members 338 and 340 may be more rigid than the membranes 334, 316. In other embodiments, the contact members 338 and 340 may be defined by a portion of the sensor membrane 334 and the flexible interface member 316, respectively. In various embodiments, only one of the membranes 334, 316 include a contact member.

As shown in FIG. 3A, the drainage catheter 302 may further include a spring 342 that acts on the flexible interface member 316 to create a chronic outward force on the flexible interface member 316, and thereby allows the flexible interface member 316 to remain extended even if the fluid pressure therein is negative. The spring 342 can have a first end 344a attached to an interior wall of the drainage catheter 302 or embedded therein and a second end 344b that connects to an inner surface of the contact member 340 and/or another portion of the flexible interface member 316. In certain embodiments, the spring 342 may be a relatively long spring that is compressed significantly (e.g., 40%, 50%, or 60% of the free length of the spring) when the drainage catheter 302 is assembled with the pressure sensor 332.

FIG. 3B illustrates the drainage catheter 302 and the pressure sensor 332 as they would be configured when assembled together in a cartridge (e.g., the cartridge 124 of FIG. 1A) or other type of housing (not shown). In certain embodiments, the pressure sensor 332 can be preassembled in a housing, and the drainage catheter 302 can be subsequently attached to the housing 332. In this embodiment, the pressure sensor 332 and the housing may be reusable so that the expensive electronics of the pressure sensor 332 can be used multiple times with different drainage catheters. In other embodiments, the drainage catheter 302 can be pre-assembled with the pressure sensor 332 such that the two opposing membranes are correctly positioned with respect to each other before use. In further embodiments, the drainage catheter 302, the pressure sensor 332, and the housing that positions the catheter 302 and the pressure sensor 332 with respect to each other can be separate components that are assembled together before use of the device.

As shown in FIG. 3B, when assembled, the flexible interface member 316 and the flexible sensor membrane 334 are forced into contact, which in certain embodiments can lead to further compression of the spring 342. During use, the pressure sensor 332 measures the sum of two pressures: (1) the pressure created by the spring 342, and (2) the pressure created by the fluid within the catheter 302 acting on the flexible interface member 316. The pressure applied by the spring 342 on the flexible interface member 316 is a known value, and therefore the pressure of the fluid acting on the flexible interface member 316 can be determined be subtracting the spring pressure from the overall pressure measured by the pressure sensor 332. This calculation can be performed automatically via a processor and/or manually by the user based on the pressure readings of the pressure sensor 332.

In certain embodiments, the spring pressure is known based on previous testing performed during assembly or product specifications. In other embodiments, the spring pressure and spring properties are unknown before use. In this embodiment, the pressure or force applied by the spring on the flexible interface member 316 can be determined by measuring the pressure via the pressure sensor 332 when the fluid pressure within the drainage catheter 302 is zero. For example, the sensor reading must be taken before implantation of the drainage catheter 302 and/or after implantation by disconnecting the portion of the drainage catheter 302 with the flexible interface member 316 from the fluid source and connecting it to the surrounding air pressure (i.e., a zero point calibration). In further embodiments, such as when the drainage catheter 302 cannot be disconnected from the fluid source, the spring pressure can be determined if certain properties of the spring are known. For example, the degree of compression of the spring 342 may be known (e.g., based on the mechanical arrangement of the spring 342 against a hard stop), and the force contributed by the spring can be known at any condition using the spring properties (e.g., the spring constant) and Hooke's Law. In this embodiment, using a significantly compressed spring (e.g., 50% of its free length) can reduce measurement errors since small errors in the measured mechanical position result in only small changes in spring force.

The outward force provided by the spring 342 on the interface member 316 allows the pressure sensor 332 to measure negative pressures within the drainage catheter 302 down to the level at which the negative pressure overcomes the spring force. The drainage catheter 302 can be designed such that the spring force is sufficient to measure a desired range of negative pressures. For example, when used for ICP measurements, it may be desirable to measure pressures of about −30 cm of water, and the spring 342 and the flexible interface member 316 size can be selected such that the spring has sufficient force to maintain contact between the flexible interface member 316 and the opposing sensor membrane 334 under this condition. In other embodiments, the drainage catheter 302 can be configured to have higher or lower threshold pressures depending on the application. This ability to measure negative pressures provided by the outwardly biased interface member 316 increases both the range of pressure values that can be measured using the drainage system and the mobility of drainage systems as a whole because the sensors are less limited by their position relative to the patient. For example, when the patient is lying down, the sensor 332 can be positioned vertically above the patient at chest or eye level with a clinician to facilitate monitoring the pressure measurements.

In various embodiments, the pressure sensor 332 can be replaced by a force sensor that measures the force acting on the flexible interface member 316. FIG. 3C, for example, is a is a side view of the drainage catheter 302 assembled with a force sensor 350 configured in accordance with an embodiment of the present technology. The force sensor 350 measures the sum of two forces: 1) the force created by the spring 342, and 2) the force created by the fluid pressure acting on the flexible interface member 316. If the force sensor 350 also has a spring-like behavior (e.g., a load cell), this force also contributes to the signal response measured by the force sensor 350 because the position of the flexible interface member 316 changes with changes in pressure, and is taken into account when determining the force or pressure the fluid applies to drainage catheter 302 with the flexible interface member 316 from the fluid source and connecting it to the surrounding air pressure (i.e., a zero point calibration).

In certain embodiments, the spring 342 can be removed and tension or elastic force from the flexible interface member 316 itself may act in place of the spring force. For example, pressing the force sensor 350 (FIG. 3C) or the pressure sensor 332 (FIG. 3B) against the flexible interface member 316 can create a tension force or elastic force on the flexible interface member 316. When a negative pressure is experienced, this tension force or elastic force acts to resist collapse of the flexible interface member 316, just as the spring 342 does as described above with reference to FIGS. 3A-3C. In this embodiment, the properties of the flexible interface member 316 may change over time. For example, the tensile or elastic forces in the flexible interface member 316 may lessen over time so the forces provided by the flexible interface member 316 can be measured periodically to ensure sufficient outward force. Similar to the spring 342, when the membrane properties of the flexible interface member 316 are unknown (either initially or over a period of time), the system can be "zeroed" by disconnecting the portion of the drainage catheter 302 with the flexible interface member 316 from the fluid source and connecting it to the surrounding air pressure (i.e., a zero point calibration) to determine the membrane properties.

Figure 4:
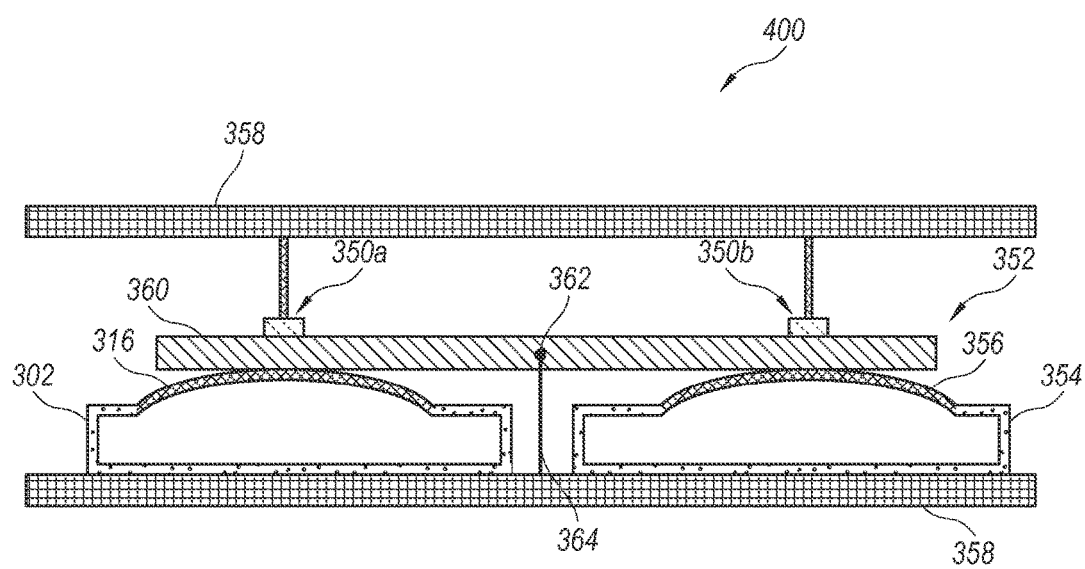
FIG. 4 is a cross-sectional view of a drainage catheter and a sensor assembly of a body fluid drainage system and a sensor assembly configured in accordance with another embodiment of the present technology.

FIG. 4 is a cross-sectional view of the drainage catheter 302 and a sensor assembly 352 of a body fluid drainage system 400 ("drainage system 400") configured in accordance with another embodiment of the present technology. The drainage system 400 includes the drainage catheter 302 with the flexible interface member 316, a fluid-filled tube 354 or other enclosure with a flexible reference membrane 356 protruding therefrom, and a housing 358 carrying the catheter 302 and the tube 354 such that the flexible interface member 316 and the reference membrane 356 are positioned adjacent to each other. In certain embodiments, the fluid-filled tube 354 can be defined by the reference lines 104 and 204 described above with reference to FIGS. 1A-2D.

In the embodiment illustrated in FIG. 4, the flexible interface member 316 of the drainage catheter 302 is not outwardly biased by an internal spring, but instead maintains connection with a lever 360 that is fixedly attached (e.g., bonded) to the flexible interface member 316 and the flexible reference membrane 356. The lever 360 can be attached to the housing 358 at a pivot point 362 via a shaft 364 such that the lever 360 pivots as the pressure within the flexible interface member 316 changes. The drainage system 400 further includes a first force sensor 350a and a second force sensor 350b (collectively referred to as force sensors 350) positioned on the opposite side of the lever 360 as the two membranes and attached to the housing 358 and configured to measure the changes in force applied by the flexible interface member 316 and the reference membrane 356 on the lever 360. As shown in FIG. 3B, when the housing 358 is assembled the first force sensor 350a presses against the lever 360 opposite the flexible interface member 316, and the second force sensor 350b presses against the lever 360 opposite the reference membrane 356. The first and second force sensors 350a and 350b can be load cells and/or other suitable types of force or pressure sensors that measure the force or pressure applied against the lever 360 by the flexible interface member 316 and the reference membrane 356.

As the pressure changes within the drainage catheter 302, the lever 360 pivots about the pivot point 362 and remains connected to the flexible interface member 316 and the adjacent reference membrane 356. These changes in position of the lever 360 caused by the force of the flexible interface member 316 and the reference membrane 356 are detected by the force sensors 350, and the detected force measurements can be used to determine the pressure or force applied by the fluid on the flexible interface member 316. For example, the difference in the force measurement taken from the first force sensor 350a and the force measurement taken from the second force sensor 350b correlates to the force applied by the fluid on the flexible interface member 316. As described above, this force measurement can be used to determine the pressure at a drainage site. In addition, because the lever 360 is attached to the flexible interface member 316 and the reference membrane 356, the lever 360 prevents the flexible interface member 316 from collapsing when it experiences negative pressures.

Figure 5:
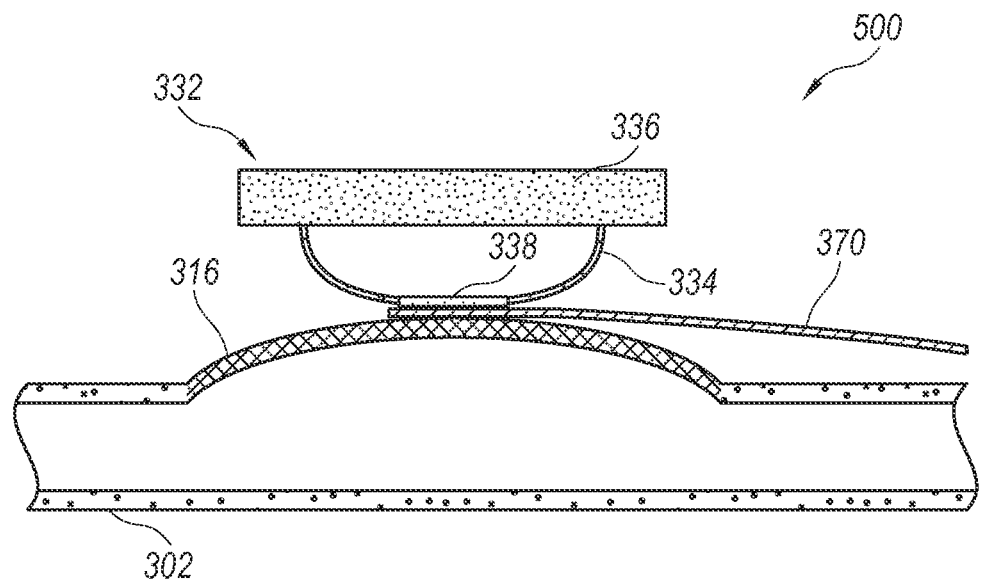
FIG. 5 is a side view of a drainage catheter and a pressure sensor of a body fluid drainage system configured in accordance with yet another embodiment of the present technology.

FIG. 5 is a side view of the drainage catheter 302 and the pressure sensor 332 of a body fluid drainage system 500 configured in accordance with yet another embodiment of the present technology. The drainage catheter 302 and the pressure sensor 332 of FIG. 5 are configured in generally the same manner as described above with reference to FIGS. 3A and 3B. In the illustrated embodiment, however, the flexible interface member 316 is outwardly biased by a lever spring 370 that is attached (e.g., bonded) to an outer surface of the flexible interface member 316. As shown in FIG. 5, for example, the lever spring 370 can be positioned between the flexible interface member 316 and the flexible sensor membrane 334 of the pressure sensor 332. The opposite end of the lever spring 370 can be attached to a portion of a housing (not shown) that carries the assembly. During use, the lever spring 370 applies a chronic outward force on the flexible interface member 316 to maintain contact between the flexible interface member 316 and the flexible sensor membrane 334 such that the pressure sensor 332 can measure negative pressures in the drainage catheter 302. In other embodiments, the pressure sensor 332 can be replaced by a force sensor (e.g., the force sensors 350 described above).

Figure 6:
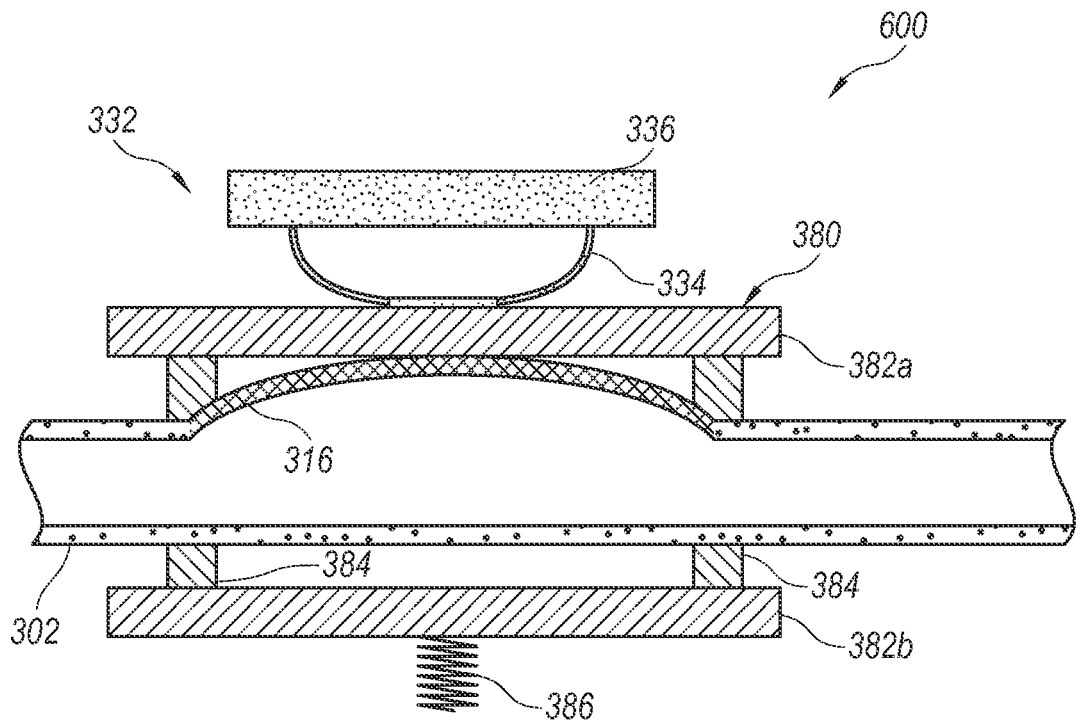
FIG. 6 is a side view of a drainage catheter and a pressure sensor of a body fluid drainage system configured in accordance with a further embodiment of the present technology.

FIG. 6 is a side view of the drainage catheter 302 and the pressure sensor 332 of a body fluid drainage system 600 configured in accordance with a further embodiment of the present technology. The drainage catheter 302 and the pressure sensor 332 of FIG. 6 are configured in generally the same manner as described above with reference to FIGS. 3A and 3B. The drainage system 600 of FIG. 6, however, includes an external spring 386 that is operably coupled to the exterior of the flexible interface member 316 and applies the chronic outward force to the flexible interface member 316. In the illustrated embodiment, for example, the spring 386 can be attached to a housing (not shown) that carries the drainage catheter 302 and the pressure sensor 332, and a connection assembly 380 is attached to the spring 386 to couple it to the exterior surface of the flexible interface member 316. The connection assembly 380 includes a first support member 382a attached (e.g., bonded) to the exterior surface of the flexible interface member 316 and positioned between the flexible interface member 316 and the flexible sensor membrane 334, and a second support member 382b attached (e.g., bonded) to the spring 386. One or more shafts 384 can extend around the drainage catheter 302 to connect the first and second support members 382a and 382b. The spring 386 can be configured to apply a chronic force against the second support member 382b (i.e., upward relative to the page), and this force can be transferred to the flexible interface member 316 via the connection assembly 380 such that the flexible interface member 316 does not collapse under negative pressures. In other embodiments, the pressure sensor 332 can be replaced by a force sensor (e.g., the force sensors 350 described above).

Figure 7:
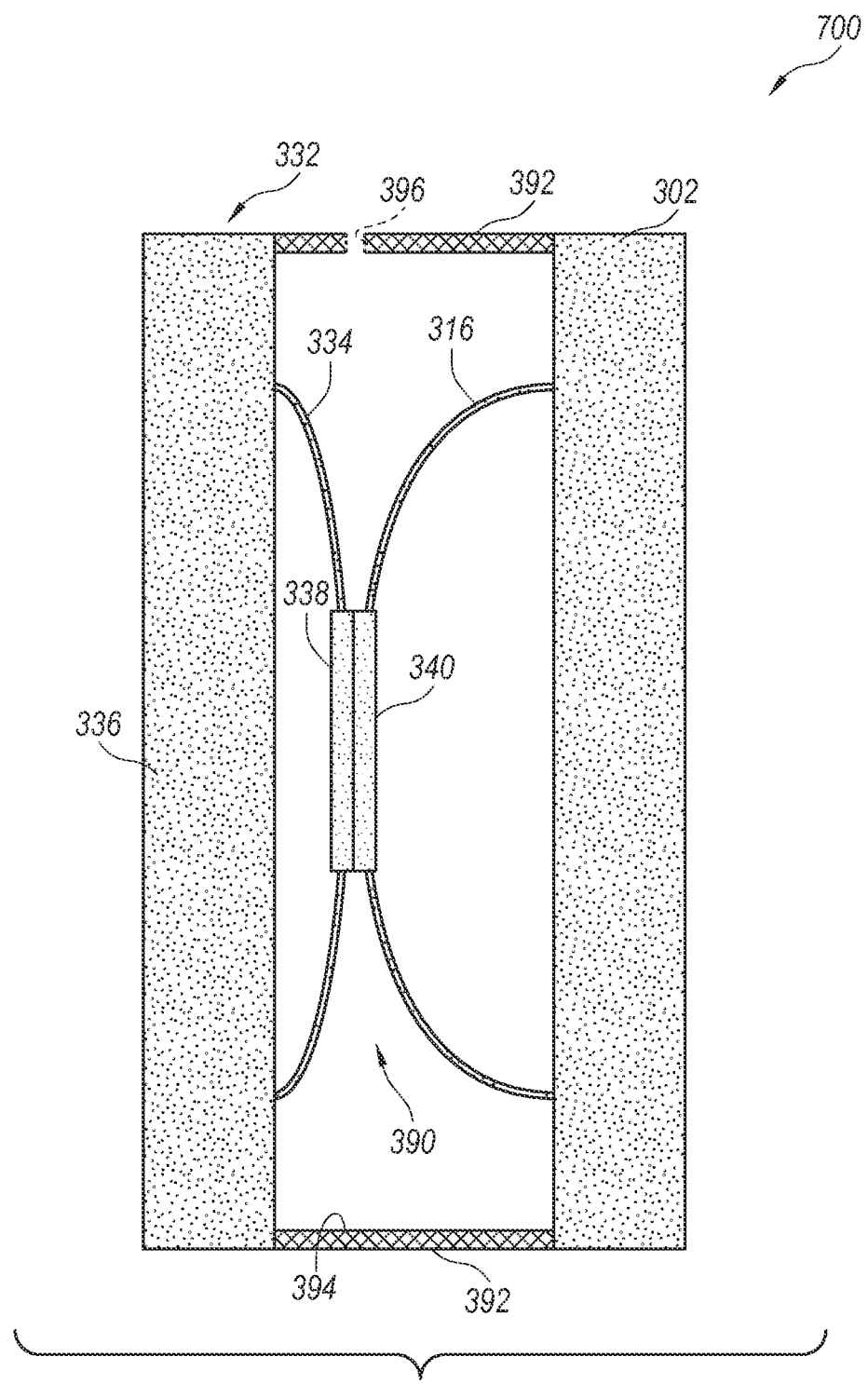
FIG. 7 is a side view of a drainage catheter and a pressure sensor of a body fluid drainage system configured in accordance with a still further embodiment of the present technology.

FIG. 7 is a side view of the drainage catheter 302 and the pressure sensor 332 of a body fluid drainage system 700 configured in accordance with a still further embodiment of the present technology. The drainage catheter 302 and the pressure sensor 332 of FIG. 7 are configured in generally the same manner as described above with reference to FIGS. 3A and 3B. The drainage system 700 of FIG. 7, however, maintains contact between the flexible interface member 316 and the opposing flexible sensor membrane 334 by creating a vacuum 390 between the flexible interface member 316 and the sensor membrane 334. For example, a housing 392 carrying the drainage catheter 302 and the pressure sensor 332 can form a sealed compartment 394 around the flexible interface member 316 and the sensor membrane 334. The compartment can be sealed from the external atmosphere via O-rings and/or other suitable features that create a seal. Once the flexible interface member 316 and the sensor membrane 334 are positioned within the sealed compartment 394, a vacuum can be applied to the space within the compartment to create a vacuum between the opposing membranes 316 and 334. For example, the housing 392 can include a sealable opening 396 through which the sealed compartment 394 can be accessed and the vacuum applied. The vacuum 390 suctions the flexible interface member 316 and the sensor membrane 334 together such that they maintain contact even when the flexible interface member 316 is under negative pressure, and therefore allows the drainage system 700 to measure negative pressures in the drainage catheter 302 via the flexible interface member 316. In other embodiments, the pressure sensor 332 can be replaced by a force sensor (e.g., the force sensors 350 described above).

In further embodiments, the drainage system 700 described above can maintain contact between the flexible interface member 316 and the opposing sensor membrane 334 using physical features that apply an attractive force between the opposing membranes 316 and 334, rather than with a vacuum. For example, the contact member 340 of the flexible interface member 316 can include a magnet or a metal, and the contact member 338 of the sensor membrane 334 can include the other of a magnet or a metal such that the two are attracted together via a magnetic force. In other embodiments, the flexible interface member 316 and the sensor membrane 334 can be attracted together with an adhesive force, such as an adhesive on one or both of the membranes 316 and 334. In further embodiments, the flexible interface member 316 and the sensor membrane 334 can be attracted to each other via a static force. For example, polymer materials can be added to or integrated into the two membranes 316 and 334, and a static charge can be created between the membranes 316 and 334. In still further embodiments, other attractive forces can be used to maintain contact between the opposing membranes 316 and 334, even under negative pressure.

The magnitude of the attractive force can be selected such that it is large enough to hold the two membranes 316 and 334 in contact over a desired range of negative pressures expected in the drainage system 700. In various embodiments, the magnitude of the attractive force can also be selected such that the flexible interface member 316 and the sensor membrane 334 can be disconnected when needed. For example, a magnetic force could be large enough to hold the two membranes 316 and 334 in contact during operation of the drainage system 700, but still allow a user to manually disconnect the two from each other (e.g., to change the drainage catheter 302, reuse a portion of the sensing device, inspect the assembly, etc.). In other embodiments, the pressure sensor 332 can be replaced by a force sensor (e.g., the force sensors 350 described above), and the attractive force can be configured to maintain contact between the force sensor and the flexible interface member 316.

Figure 8:
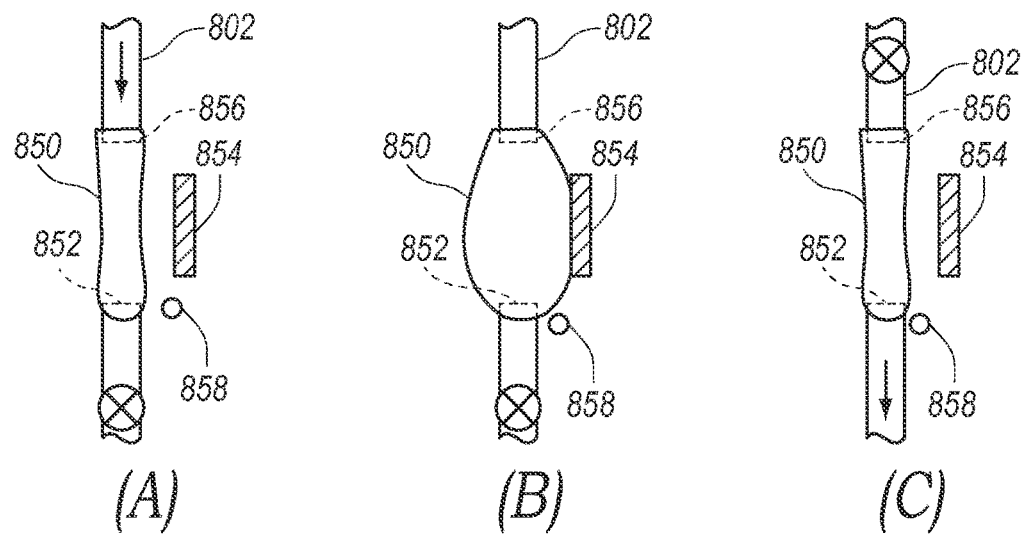
FIG. 8 is a side view of a flexible reservoir for measuring flow rate of a body fluid drainage system during various stages of filling in accordance with an embodiment of the present technology.

FIG. 8 is a side view of a flexible reservoir 850 for measuring flow rate of a body fluid drainage system during various stages of filling in accordance with an embodiment of the present technology. Flowrate of a fluid can be measured by cycling through filling and draining a reservoir of known volume. As shown in FIG. 8, the flexible reservoir 850 can be attached to a drainage catheter 802 of a body fluid drainage system (e.g., any of the drainage systems described herein). The flexible reservoir 850 can be filled by closing an outlet 852 of the reservoir 850, and a first sensor 854 (e.g., a pressure sensor, a force sensor, an infrared sensor, etc.) can be used to determine when the reservoir 850 has been filled. For example, as shown in FIG. 8, the sensor 854 can be positioned such that the first sensor 854 is spaced apart from the flexible reservoir 850 when the reservoir 850 is in an uninflated state (as shown in the illustration above (A)) and contact the reservoir 850 when the reservoir 850 is full (as shown in the illustration above (B)). When the first sensor 854 detects that the reservoir 850 has contacted the sensor 854 or pressed against it to a desired degree, the first sensor 854 can indicate that the reservoir is full. Once full, the outlet 852 opens allowing the fluid to drain out of the reservoir 850. An inlet 856 of the reservoir 850 can be closed or open during drainage.

The system can further include a second sensor 858 that determines when drainage is complete. In other embodiments, a single sensor can be used to determine whether the reservoir 850 is full or drained. In various embodiments, drainage of the reservoir 850 can be assisted by compressing the flexible reservoir 850 (e.g., manually or with an automated compressing mechanism).

The flowrate through the drainage catheter 802 can be determined based on the known volume of the reservoir 850 and the number of times the reservoir 850 is drained within a predetermined period of time. In other embodiments, the first sensor 854, the second sensor 858, and/or another sensor can measure the degree of filling of the reservoir 850 to provide a continuous measurement of the rate the reservoir 850 is filled, and thus a continuous flowrate measurement. The first sensor 854, the second sensor 858, and/or other sensors used in conjunction with the filling of the reservoir 850 can include optical sensors, capacitive sensors, conductivity sensors, pressure sensors, force sensors, contact sensors, proximity sensors (e.g, magnetic, capacitive), ultrasonic sensors, etc.

Figure 9:
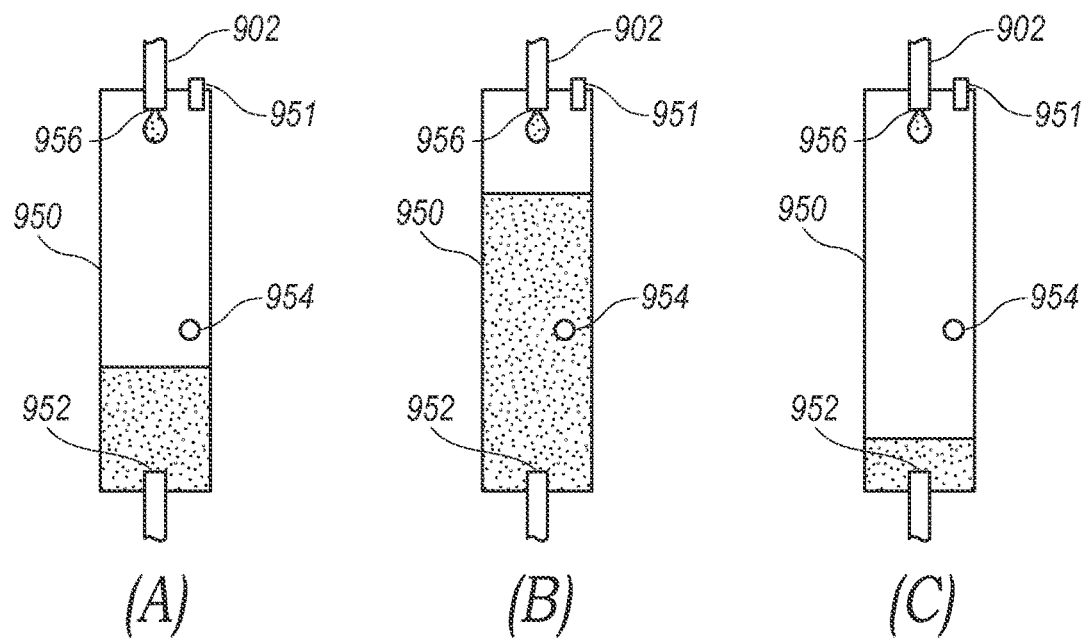
FIG. 9 is a side view of a rigid reservoir for measuring flow rate of a body fluid drainage system during various stages of filling in accordance with an embodiment of the present technology.

Selected Embodiments of Systems for Measuring Flow Rate in Body Fluid Drainage Systems FIG. 9 is a side view of a rigid reservoir 950 for measuring flow rate of a body fluid drainage system during various stages of filling in accordance with an embodiment of the present technology. As shown in FIG. 9, the rigid reservoir 950 is in fluid communication with a drainage catheter 902 of a body fluid drainage system (e.g., any of the body fluid drainage systems described herein). As shown in FIG. 9, the rigid reservoir 950 can be a drip chamber of known volume and can include one or more sensors 954 that measure the fluid level at locations within the reservoir 950 previously identified as "full" and "empty". The reservoir 950 can also include a vent 951 at the top of the reservoir 950 to allow air to be displaced during the filling stage and to allow air to enter the reservoir 950 during the drainage stage. The air vent 951 can have a membrane or filter (not shown) to prevent contamination of the fluid (e.g., a porous membrane made of Teflon, manufactured by E. I. DuPont De Nemours and Company of Wilmington, Del.).

During the fluid accumulation phase (represented by the illustration in FIG. 9 above (A)), an outlet 952 of the reservoir 950 is closed and the fluid level rises during flow. When the fluid level reaches the "full" point, the system opens the outlet 952 to allow the fluid to drain out of the reservoir 950 (represented by the illustration above (B)). During this drainage stage, an inlet 956 of the reservoir 950 can be open or closed. When the fluid reaches the "empty" point, the system closes the outlet 952 and resumes the accumulation or filling phase. The flowrate of the fluid through the drainage catheter 902 can be calculated based on the known volume of the reservoir 950 and the number of times the fluid is drained from the reservoir 950 in a given time period. Alternatively, the sensor 954 can measure the degree of filling of the reservoir 950 to allow a continuous measurement of the filling rate, and thus a continuous flowrate measurement. For example, the sensor 954 can be configured to intermittently or continuously measure the location of the fluid level within the reservoir 950, or multiple sensors 954 can be positioned along the height of the reservoir 950 to provide semi-continuous measurement of the filling state of the reservoir 950. The sensor 954 or sensors can include optical sensors, capacitive sensors, conductivity sensors, pressure sensors (measuring the fluid head in the reservoir), ultrasonic sensors, etc.

Selected Embodiments of Body Fluid Drainage Systems

Figure 10:
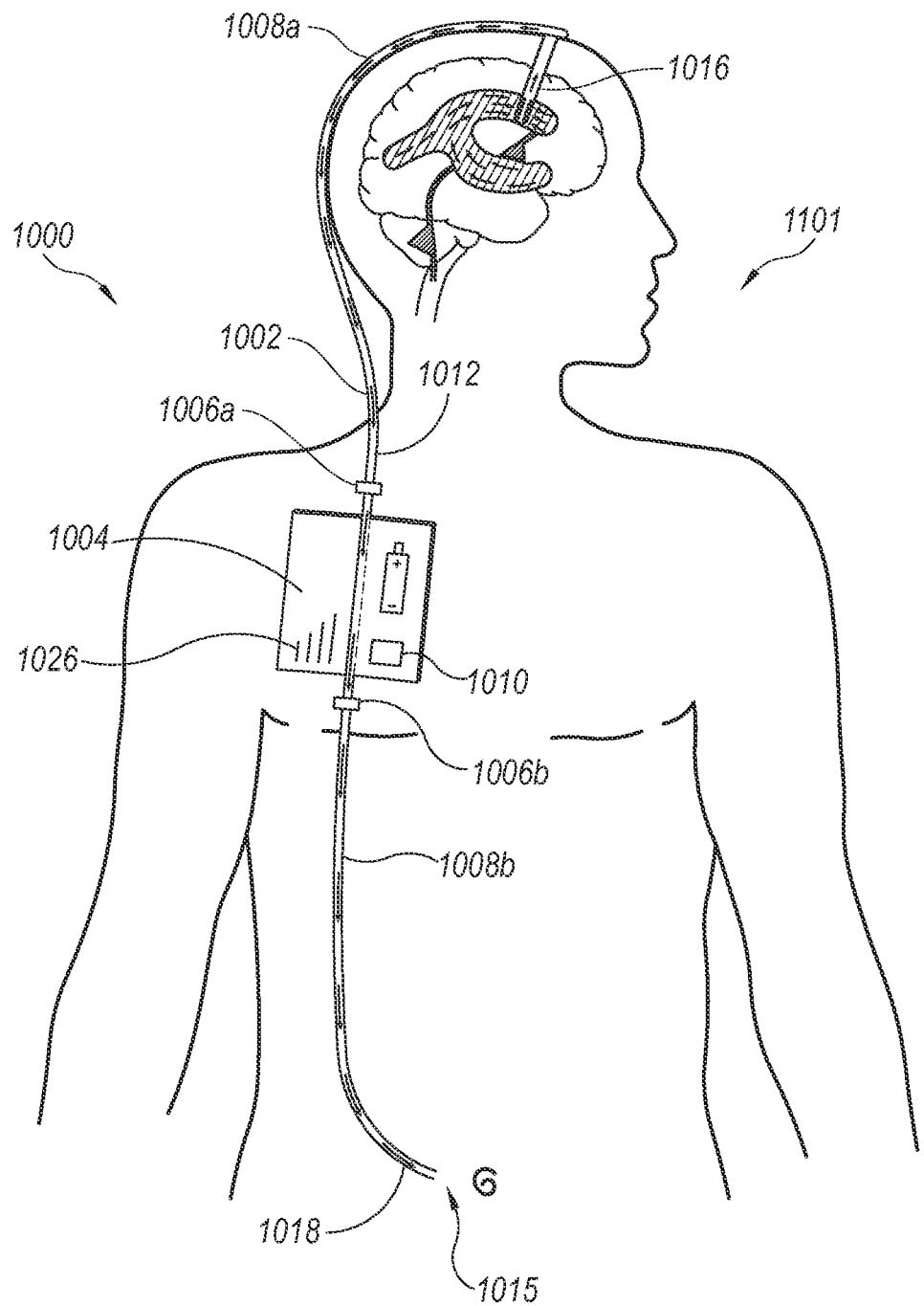
FIG. 10 is a partially schematic illustration of an internal body fluid drainage system installed within a patient in accordance with an embodiment of the present technology.

FIG. 10 is a schematic view of an internal body fluid drainage system 1000 ("drainage system 1000") implanted in a patient 1001 in accordance with an embodiment of the present technology. The drainage system 1000 can include a catheter 1002, a valve device 1004 acting on an exterior surface 1012 of the catheter 1002, and one or more sensors 1006 (identified individually as a first sensor 1006a and a second sensor 1006b). The drainage system 1000 can also include a controller 1010 (e.g., a controller of a CPU) that is operatively coupled to the valve device 1004 and/or the sensors 1006. The valve device 1004 can apply incremental forces to the exterior surface 1012 of the catheter 1102 to regulate body fluid flow through the catheter 1002, and the controller 1010 can alter the level of force applied by the valve device 1004 on the catheter 1002 in response to measurements (e.g., force, pressure, flow rate, etc.) taken from the sensors 1006.

As shown in FIG. 10, the catheter 1002 can include a proximal portion 1008a and a distal portion 1008b opposite the proximal portion 1008a. The catheter 1002 can be made from a range of polymers, such as silicone, latex, thermoplastic elastomers, and/or other suitable tubing materials. In selected embodiments, portions of the catheter proximate to the valve device 1004 can include compressible peristaltic pump tubing (e.g., silicone rubber, polyvinyl chloride), reduced fouling surfaces, tubing with different mechanical compliances, and/or other durable elastomeric materials that resist fatigue. In other embodiments, the catheter 1002 can be made from tubing with biocides and/or other anti-biofouling agents that prevent organisms from entering the drainage system 1000 and causing infection.

The proximal portion 1008a of the catheter 1002 is positioned at a site of excess body fluid and the distal portion 1008b can be placed in fluid communication with an internal receptacle that collects and/or absorbs the body fluid. The proximal portion 1008a of the catheter 1002 can include an inlet region 1016 with one or more openings (not visible) in fluid communication with a site of excess body fluid such that the body fluid can flow into the catheter 1002. In the embodiment illustrated in FIG. 10, for example, the inlet region 1016 of the catheter 1002 is installed (e.g., via a burr hole) into the lateral ventricles 1013 of the patient's brain to receive excess CSF. After entering the drainage system 1000, the body fluid can travel in an antegrade flow through the catheter 1002 to the distal portion 1008b. The distal portion 1008b can include an outlet region 1018 that expels the excess body fluid into an internal location. For example, the outlet region 1018 can be placed in fluid communication with the patient's peritoneal cavity 1015, where excess body fluid can reabsorb into the body. In other embodiments, the outlet region 1018 can expel the body fluid into the atrium of the heart, the pleural lining of the lung, the gallbladder, and/or other suitable terminal locations.

The valve device 1004 can be positioned between the proximal and distal portions 1008a and 1008b of the catheter 1002 to regulate the body fluid flow through the drainage system 1000. As shown in FIG. 10, for example, the valve device 1004 can be implanted in a subclavicular pocket of the patient 1001. In other embodiments, the valve device 1004 can be installed in a prefascial or subfascial intra-abdominal region. This intra-abdominal positioning is particularly suited for neonates to ease exchange of the valve device 1004 as the child grows, but also facilitates accessibility to the valve device 1004 for adults. Advantageously, placement of the valve device 1004 in either the subclavicular pocket or the intra-abdominal region negates the need to shave the patient's scalp to perform cranial surgery in the event that a component requires replacement or repair, and thus avoids the need for repeated incisions in the scalp that can cause devascularization, poor wound healing, and/or infection. The intra-abdominal valve device 1004 also eases the periodic replacement of batteries or other power sources. In other embodiments, the valve device 1004 can be installed subcutaneously in other regions of the torso or between another site of excess body fluid and a receptacle that can collect and/or reabsorb the body fluid. In further embodiments, the valve device 1004 can be miniaturized such that it can be implanted under the scalp.

As shown in FIG. 10, the sensors 1006 can be positioned proximate to the outlet and inlet to the valve device 1004. Accordingly, the first sensor 1006a can measure the flow rate and/or the pressure within the proximal catheter 1008a before it enters the valve device 1004 and the second sensor 1006b can measure the flow rate and/or pressure within the distal portion 1008b as it exits the valve device 1004. This information can be used to ensure the valve device 1004 generates the desired drainage rate, to monitor patient orientation, to perform diagnostics on the drainage system, and/or derive other desired measurements or characteristics. In other embodiments, the drainage system 1000 can include more or less sensors 1006.

The sensors 1006 can also be used to derive a pressure at a desired location (e.g., in the patient's brain at the Foramen of Monroe for ICP) spaced apart from the sensors 1006. For example, the sensors 1006 that are positioned proximate to the valve device 1004 in the torso of the patient 1001 can be used to derive ICP. As shown in FIG. 10, the sensors 1006 can be positioned on either side of the valve device 1004 to measure pressure upstream and downstream of the valve device 1004. When the patient 1001 is upright (i.e., standing), the first sensor 106a at the proximal portion 1008a can measure a pressure that is substantially equal to the ICP plus the pressure head created by the body fluid in the proximal portion 1008a above the first sensor 1006a. The second sensor 1006b at the distal portion 1008b can measure a pressure substantially equal to the pressure at the outlet region 1018 (e.g., the peritoneal cavity 1015; as is known in the art, the pressure is approximated as zero relative to atmosphere) plus the negative pressure created by the body fluid in the distal portion 1008b below the second sensor 1006b. The pressures from the upstream and downstream sensors 1006 can be combined to derive the true ICP. For example, when the valve device 1004 is positioned midway between the ventricle 1013 and the outlet region 1018, the summation of the two pressure measurements from the sensors 1006 negates the contribution of pressure head and provides the true ICP.

The controller 1010, e.g., a microprocessor, can read the measurements taken from the sensors 1006 (e.g., pressure, flow rate, orientation, etc.), store such measurements and other information in a database, adjust the position of the valve device 1004, and/or carry out algorithms to regulate fluid flow through the drainage system 1000. For example, the controller 1010 can compare pressure measurements from the sensors 1006 with a desired ICP to determine whether to incrementally open or close the valve device 1004 and by what percentage. For example, when the pressure is lower than a desired pressure, the controller 1010 can incrementally close the valve device 1004 to increase the resistance to antegrade flow through the catheter 1002. If the sensed pressure is higher than desired, the controller 1010 can incrementally open the valve device 1004 to decrease the resistance to antegrade flow. Similarly, the controller can also compare the sensed flow rate with a desired flow rate, and adjust the position of the valve device 1004 accordingly. The controller 1010 can also carry out an algorithm that moves the valve device 1004 a predetermined amount each time a measurement outside of a desired limit (e.g., desired CSF range) is detected. Such a control algorithm can also relate the incremental movement of the valve device 1004 to the magnitude of the difference between a desired and a measured value. In other embodiments, a proportional-integral-derivative ("PID") control algorithm or variations thereof (e.g., P-only, PI-only) can control the movement of the valve device 1004. As such, the controller 1010 can manage body fluid flow in real-time to maintain the ICP and/or other desired parameter within appropriate limits across a range of changes in pressure or body fluid generation rate caused by physiologic processes (e.g., valsalva maneuvers, changes in body orientation).

Additionally, the controller 1010 can also include logic to clear the valve device 1004 of obstructions by incrementally opening the valve device 1004 until the obstruction clears. For example, the controller 1010 can be configured to maintain a desired ICP such that when an obstruction within the valve device 1004 causes an increase in the measured pressure, the control algorithm (e.g., a proportional-integral-derivative) incrementally or fully opens the valve device 1004 to decrease the resistance to antegrade flow. This incremental opening of the valve device 1004 allows the obstruction to flow through the valve device 1004 such that the drainage system 1000 can maintain the desired ICP. As described in further detail below, in other embodiments, the controller 1010 can include logic that clears and/or prevents obstructions by flushing the catheter 1002 with body fluid.

In selected embodiments, the controller 1010 can be operatively coupled to a wireless communication link 1026, such as a WiFi connection, radio signal, and/or other suitable communication links that can send and/or receive information. The wireless communication link 1026 allows measurements from the sensors 1006 and/or other information to be monitored and/or analyzed remotely. For example, the wireless communication link 1026 allows measurements recorded from the sensors 1006 to be accessed at a doctor's office, at home by the patient 1001, and/or at other remote locations. Additionally, the drainage system 1000 can use the wireless communication link 1026 to receive information at a WiFi hot spot or other remotely accessible locations. This allows a remote physician to inquiry the drainage system 1000 regarding particular measurements (e.g., ICP), instruct the controller 1010 to adjust the valve device 1004 accordingly, and/or program sophisticated algorithms onto the controller 1010 for the drainage system 1000 to carry out. Accordingly, the drainage system 1000 can provide more expedient, sophisticated, and personalized treatment than conventional CSF shunts, without requiring frequent in-office visits.

Figure 11:
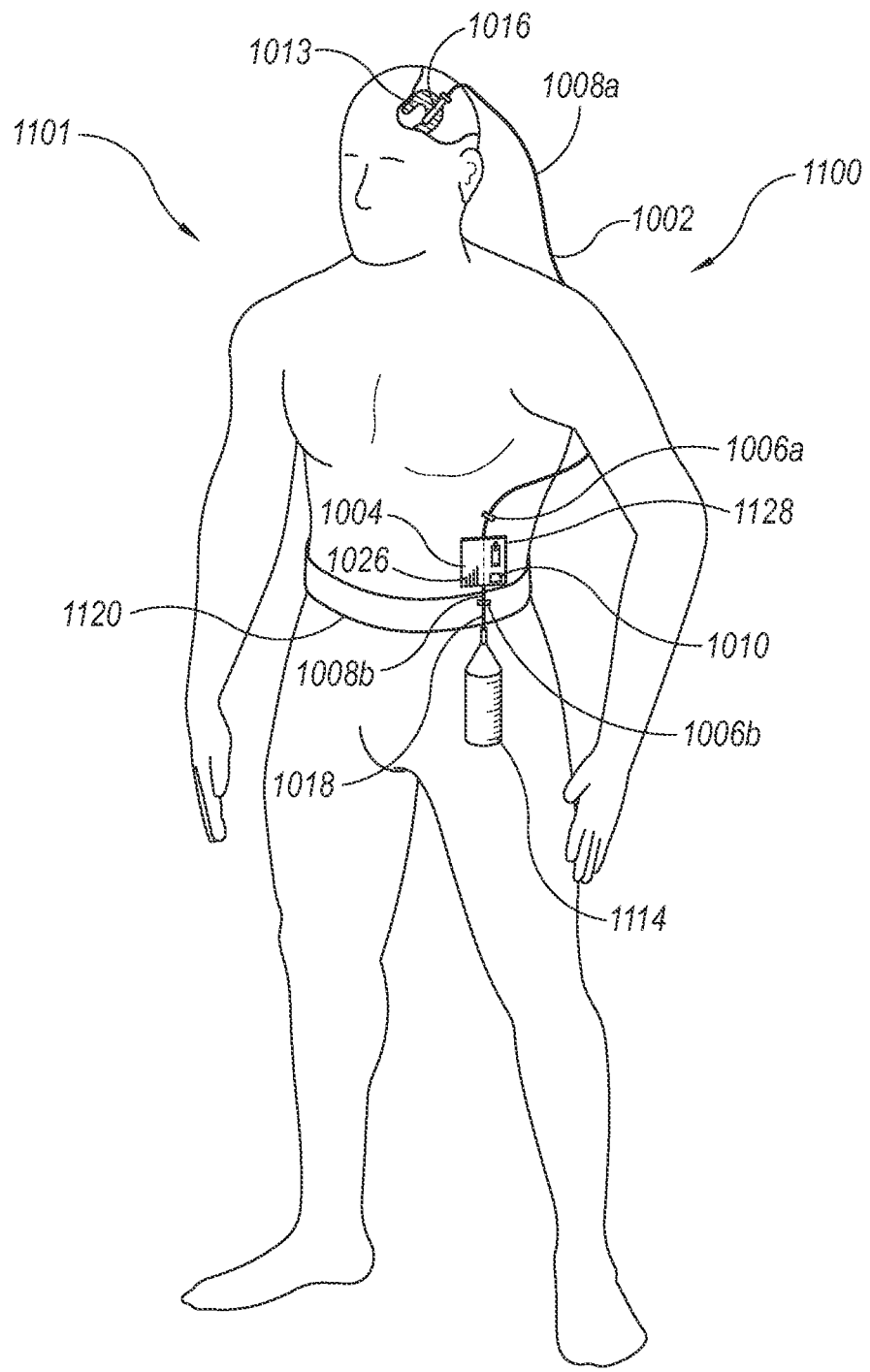
FIG. 11 is a partially schematic illustration of an external body fluid drainage system installed in a patient in accordance with an embodiment of the present technology.

FIG. 11 is a schematic view of an external body fluid drainage system 1100 ("drainage system 1100") implanted in the patient 1101 in accordance with an embodiment of the present technology. The drainage system 1100 includes features generally similar to the drainage system 1000 described above with reference to FIG. 10. For example, the drainage system 1100 can include the catheter 1002 having the proximal portion 1008a and the distal portion 1008b, the valve device 1004 positioned therebetween, the sensors 1006, and the controller 1010 operatively coupled to the sensors 1006 and the valve device 1004. Additionally, like the internal drainage system 1000 described above, the external drainage system 1100 can regulate CSF or other excess body fluid flow using sophisticated and individualized methods. However, the drainage system 1100 shown in FIG. 11 is installed externally, between the ventricle 1013 and an external receptacle 1114. The external receptacle 1114 can be placed in fluid communication with the outlet region 1018 of the catheter 1002 such that it can collect the excess body fluid. As such, the external receptacle 1114 can be a bag or container made from a range of polymers (e.g., silicone, polyvinyl chloride) and/or other suitable materials for storing body fluids.

In the illustrated embodiment, the external receptacle 1114 is secured to the midsection of the patient 1101 with a belt 1120 such that the patient 1101 can remain mobile as the drainage system 1100 removes the excess body fluid. As shown in FIG. 11, the belt 1120 can also carry a housing 1128 that contains the valve device 1004, the controller 1010, and/or other devices that operate the drainage system 1100. The externally positioned housing 1128 can be made from a durable material (e.g., plastic) that can withstand the rigors of the outside environment and substantially protect the components within.

In various embodiments, such as when the drainage system 1100 is used for temporary shunting of acute accumulation of the body fluid, the external receptacle 1114 can be hung on a pole commonly used for IV bags or otherwise affixed to an external structure. Additionally, for temporary drainage, the devices within the housing 1128 can also be positioned apart from the patient 1101, such as on a console connected with a power source.

In various embodiments, the drainage system 1000 and 1100 of FIGS. 10 and 11 can further include the pressure reference lines 104 and 204 and associated features described above with reference to FIGS. 1A-2D, the features that allow for negative pressure measures in a drainage catheter as described above with reference to FIGS. 3A-7, and/or the reservoirs 850 and 950 for determining flow rate through drainage catheters as described with reference to FIGS. 8 and 9.

EXAMPLES

1. A pressure reference assembly for a body fluid drainage system, the pressure reference assembly comprising:
  a first reference line having a first end portion and second end portion, wherein the first end portion of the first reference line comprises a first flexible region configured to be in pressure communication with a corresponding flexible portion of a drainage catheter, and wherein the first reference line is configured to be filled with a fluid;
  a second reference line having a first end portion and a second end portion, wherein the first end portion of the second reference line comprises a second flexible region configured to be in pressure communication with atmospheric pressure, wherein the second reference line is configured to be filled with the fluid, and wherein the first end portions of the first and second reference lines are configured to be positioned at a first location and the second end portions of the first and second reference lines are configured to be positioned at a second location spaced apart from the first location; and
  a sensor assembly at the second portions of the first and second reference lines, wherein the sensor assembly is configured to measure pressure and/or force at the second portions of the first and second reference lines to determine pressure at the proximal portion of the drainage catheter.

2. The pressure reference assembly of example 1 wherein the sensor assembly comprises:
  a first pressure sensor at the second end portion of the first reference line, wherein the first pressure sensor is configured to measure pressure at the second end portion of the first reference line; and
  a second pressure sensor at the second end portion of the second reference line, wherein the second pressure sensor is configured to measure pressure at the second end portion of the second reference line.

3. The pressure reference assembly of example 2, further comprising a processing device operably coupled to the first and second pressure sensors, wherein the processing device is configured to determine intracranial pressure by subtracting a second pressure measurement taken by the second pressure sensor from a first pressure measurement taken by the first pressure sensor.

4. The pressure reference assembly of any one of examples 1-3 wherein the first end portions of the first and second reference lines are configured to be positioned near lateral ventricles of a patient's head, and wherein the second location is spaced apart from the patient's head.

5. A body fluid drainage system, comprising:
  a drainage catheter having a proximal portion and a distal portion, wherein the proximal portion comprises an inlet and a flexible interface member positioned distally with respect to the inlet, and wherein the inlet is configured to be in fluid communication with a site of excess body fluid within a patient;
  a first reference line having a first portion and a second portion opposite the first portion, wherein the first portion of the first reference line has a first flexible region configured to be in pressure communication with the flexible interface member of the drainage catheter;
  a second reference line having a first portion and a second portion opposite the first portion, wherein the first portion of the second reference line has a second flexible region configured to be in pressure communication with atmospheric pressure,
    wherein the first and second flexible regions are configured to be positioned at a first location and the second portions of the first and second reference lines are configured to be positioned at a second location spaced apart from the first location; and
  a pressure sensor assembly at the second portions of the first and second reference lines, wherein the pressure sensor assembly is configured to measure pressure at the second portions of the first and second reference lines to determine pressure at the proximal portion of the drainage catheter.

6. The body fluid drainage system of example 5 wherein the first and second reference lines are filled with a reference fluid, and wherein the reference fluid comprises silicone oil, mineral oil, and/or propylene glycol.

7. The body fluid drainage system of example 5 or 6 wherein the first and second flexible regions each comprise a flexible membrane made of an ether- and/or ester-based material.

8. The body fluid drainage system of any one of examples 5-7 wherein the pressure sensor assembly comprises:
- a first pressure sensor at the second portion of the first reference line, wherein the first pressure sensor is configured to measure pressure of the first reference line at the second location; and
- a second pressure sensor at the second portion of the second reference line, wherein the second pressure sensor is configured to measure pressure of the second reference line at the second location.

9. The body fluid drainage system of example 8, further comprising a processing device operably coupled to the first and second pressure sensors, wherein the processing device is configured to use measured pressures of the first and second sensors to derive the intracranial pressure of the patient when the first location is proximate to lateral ventricles of the patient's head.

10. The body fluid drainage system of any one of examples 5-9 wherein the pressure sensor assembly comprises a pressure sensor at the second location and operably coupled to the first and second reference lines, wherein the pressure sensor is configured to measure differential pressure between the first reference line and the second reference line.

11. The body fluid drainage system of any one of examples 5-10 wherein the flexible interface member and the first flexible region are attached together.

12. The body fluid drainage system of any one of examples 5-11 wherein the drainage catheter further comprises a spring at the proximal portion and operably coupled to the flexible interference member, wherein the spring is configured to create an outward force on the flexible interface member to maintain contact with the first flexible region of the first reference line.

13. The body fluid drainage system of example 12 wherein the spring has a free length, and wherein the spring is compressed at least 50% of the free length when in the flexible interface member is at atmospheric pressure.

14. The body fluid drainage system of any one of examples 5-13, further comprising:
- a support member attached to an external surface of the flexible interface member; and
- a spring acting on the support member, the spring and the support member together applying a chronic outward force on the flexible interface member to maintain contact with the first flexible region of the first reference line.

15. The body fluid drainage system of any one of examples 5-14, further comprising a leaf spring connected to an external surface of the flexible interface member and configured to create an outward force on the flexible interface member to maintain contact with the first flexible region of the first reference line.

16. The body fluid drainage system of any one of examples 5-15 wherein the flexible interface member has an elastic and/or tension force in an unloaded state that creates an outward force on the flexible interface member to maintain contact with the first flexible region of the first reference line.

17. The body fluid drainage system of any one of examples 5-16 wherein the flexible interface member and the first flexible region are connected together via a magnetic force, an adhesive force, and/or a static force.

18. The body fluid drainage system of any one of examples 5-17 wherein the flexible interface member and the first flexible region are positioned within a sealed compartment and connected together via a vacuum in the sealed compartment.

19. A body fluid drainage system, comprising:
- a drainage catheter having a proximal portion and a distal portion, wherein the proximal portion comprises an inlet configured to be in fluid communication with a site of excess body fluid within a patient, and wherein the site of excess body fluid defines a point along a reference axis that extends through the site of excess body fluid;
- a first reference line having a first end portion and a second end portion opposite the first end portion, wherein the first end portion of the first reference line has a first flexible region configured to be in pressure communication with atmospheric pressure, and wherein the first flexible region is configured to be positioned at a first location along the reference axis to one side of the inlet of the drainage catheter;
- a second reference line having a first end portion and a second end portion opposite the first portion, wherein the first end portion of the second reference line has a second flexible region configured to be in pressure communication with atmospheric pressure, and wherein the second flexible region is configured to be positioned at a second location along the reference axis to a side of the inlet of the drainage catheter opposite the first flexible region,
  wherein the second end portions of the first and second reference lines are configured to be positioned at a third location spaced apart from the first and second locations; and
- a pressure sensor assembly at the third location and operably coupled to the distal portion of the drainage catheter and the second portions of the first and second reference lines, wherein the pressure sensor assembly is configured to measure pressure at the distal portion of the drainage catheter and at the second end portions of the first and second reference lines to determine pressure at the site of excess body fluid.

20. The body fluid drainage system of example 19 wherein the reference axis extends through lateral ventricles in a head of the patient, and wherein the first end portion of the first reference line is configured to be positioned on a first side of the head, and wherein the first end portion of the second reference line is configured to be positioned on a second side of the head opposite the first side.

21. The body fluid drainage system of example 19 or 20 wherein the first end portions of the first and second reference lines are spaced apart from the site of excess body by an equal distance.

22. The body fluid drainage system of any one of examples 19-21 wherein the first end portion of the first reference line is spaced apart from the site of excess body fluid by a first distance along the reference axis, and wherein the first end portion of the second reference line is spaced apart from the site of excess body fluid by a second distance along the reference axis different than the first distance.

23. The body fluid drainage system of any one of examples 19-22 wherein the first and second reference lines are filled with a reference fluid.

24. The body fluid drainage system of any one of examples 19-23 wherein:
- the distal portion of the drainage catheter comprises a flexible interface member at the third location; and the pressure sensor assembly comprises a sensor operably coupled to the flexible interface member and configured to detect pressure and/or force of the drainage catheter at the third location.

25. The body fluid drainage system of example 24 wherein the sensor is a pressure sensor having a flexible sensor membrane in contact with flexible interface member, and wherein the drainage catheter comprises a feature configured to maintain contact with the flexible sensor membrane when the flexible interface member is at a negative pressure.

26. A body fluid drainage system, comprising:
a first reference line having a first end portion and a second end portion opposite the first end portion, wherein the first end portion of the first reference line has a first flexible region configured to be in pressure communication with atmospheric pressure, and wherein the first flexible region is configured to be positioned at a first location along a reference axis that extends through a drainage site;
a second reference line having a first end portion and a second end portion opposite the first portion, wherein the first end portion of the second reference line has a second flexible region configured to be in pressure communication with atmospheric pressure, and wherein the second flexible region is configured to be positioned at a second location along the reference axis, and wherein the second end portions of the first and second reference lines are configured to be positioned at a third location spaced apart from the first and second locations; and
a sensor assembly at the third location and operably coupled to the second portions of the first and second reference lines, wherein the pressure sensor assembly is configured to measure pressure at the second end portions of the first and second reference lines.

27. A body fluid drainage system, comprising:
a catheter having an inlet configured to be in fluid communication with a site of excess body fluid within a patient and a flexible interface member spaced along the catheter apart from the inlet; and
a sensor operably coupled to the flexible interface member and configured to detect pressure and/or force in the catheter via displacement of the flexible interface member,
wherein the system is configured to maintain contact between the flexible interface member and the sensor when the flexible interface member is at negative pressures.

28. The body fluid drainage system of example 27, further comprising a spring within the catheter and acting on the flexible interference member to create a chronic outward force on the flexible interface member to maintain contact with sensor.

29. The body fluid drainage system of example 28 wherein the spring has a free length, and wherein the spring is compressed at least 50% of the free length when in the flexible interface member is at atmospheric pressure.

30. The body fluid drainage system of any one of examples 27-29, further comprising:
a support member attached to an external surface of the flexible interface member; and
a spring acting on the support member, the spring and the support member together applying a chronic outward force on the flexible interface member to maintain contact with the sensor.

31. The body fluid drainage system of any one of examples 27-30, further comprising a leaf spring connected to an external surface of the flexible interface member and configured to create an outward force on the flexible interface member to maintain contact with the sensor.

32. The body fluid drainage system of any one of examples 27-31 wherein the flexible interface member has an elastic and/or tension force in an unloaded state that creates an outward force on the flexible interface member to maintain contact with the sensor.

33. The body fluid drainage system of any one of examples 27-32 wherein the flexible interface member and the sensor are connected together via a magnetic force, an adhesive force, and/or a static force.

34. The body fluid drainage system of any one of examples 27-33 wherein the sensor is a force sensor with a contact member operably coupled to the flexible interface member.

35. The body fluid drainage system of any one of examples 27-35 wherein the sensor is a pressure sensor having a flexible sensor membrane operably coupled to the flexible interface member.

36. The body fluid drainage system of example 35, further comprising a housing surrounding the flexible interface member and the flexible sensor membrane to define a sealed compartment, and wherein the flexible sensor membrane and the flexible interface member are placed in contact via a vacuum in the sealed compartment.

CONCLUSION

From the foregoing, it will be appreciated that specific embodiments of the present technology have been described herein for purposes of illustration, but that various modifications may be made without deviating from the spirit and scope of the disclosure. For example, the pressure reference lines of FIGS. 1A-2D can be added to the body fluid drainage systems 1000 and 1100 shown in FIGS. 10 and 11. Additionally, the negative pressure measurement features described with reference to FIGS. 3A-7 and/or the flow rate measurement features of FIGS. 8 and 9 can be incorporated into the other drainage systems described herein. Aspects of the disclosure described in the context of particular embodiments may be combined or eliminated in other embodiments. Further, while advantages associated with certain embodiments of the disclosure have been described in the context of those embodiments, other embodiments may also exhibit such advantages, and not all embodiments need necessarily exhibit such advantages to fall within the scope of the disclosure. Accordingly, embodiments of the disclosure are not limited except as by the appended claims.

We claim:
1. A pressure reference assembly for a body fluid drainage system, the pressure reference assembly comprising:
a first reference line having a first portion and a second portion opposite the first portion, wherein the first portion of the first reference line has a first flexible region configured to sense pressure;
a second reference line having a first portion and a second portion opposite the first portion, wherein the first portion of the second reference line has a second flexible region configured to be in pressure communication with atmospheric pressure, and wherein the first and second flexible regions are configured to be positioned at a first location and the second portions of the first and second reference lines are configured to be positioned at a second location spaced apart from the first location; and
a pressure sensor assembly at the second portions of the first and second reference lines, wherein the pressure sensor assembly is configured to measure pressure and/or force at the second portions of the first and second reference lines.

2. The pressure reference assembly of claim 1, wherein the first and second reference lines are filled with a fluid.

3. The pressure reference assembly of claim 1, wherein the first flexible region of the first reference line is configured to be in pressure communication with a drainage catheter and to sense pressure within the drainage catheter.

4. The pressure reference assembly of claim 1, wherein the first flexible region of the first reference line is configured to be in pressure communication with atmospheric pressure.

5. The pressure reference assembly of claim 1, wherein the pressure sensor assembly comprises:
a first pressure sensor at the second end portion of the first reference line, wherein the first pressure sensor is configured to measure pressure at the second end portion of the first reference line; and
a second pressure sensor at the second end portion of the second reference line, wherein the second pressure sensor is configured to measure pressure at the second end portion of the second reference line.

6. The pressure reference assembly of claim 5, wherein the first flexible region of the first reference line is configured to be in pressure communication with a drainage catheter and to sense pressure within the drainage catheter, and further comprising a processing device operably coupled to the first and second pressure sensors, wherein the processing device is configured to determine pressure at the drainage catheter by subtracting a second pressure measurement taken by the second pressure sensor from a first pressure measurement taken by the first pressure sensor.

7. The pressure reference assembly of claim 1, wherein the first end portions of the first and second reference lines are configured to be positioned near lateral ventricles of a patient's head, and wherein the second location is spaced apart from the patient's head.

8. The pressure reference assembly of claim 7, wherein the first flexible region of the first reference line is configured to be in pressure communication with a drainage catheter and to sense pressure within the drainage catheter, and additionally comprising a processing device operably coupled to the pressure sensor assembly and configured to determine intracranial pressure based on a difference is pressure and/or force at the second portions of the first and second reference lines.

9. A body fluid drainage system, comprising a pressure reference assembly in combination with a drainage catheter, wherein:
the drainage catheter has a proximal portion and a distal portion, and wherein the proximal portion comprises an inlet configured to be in fluid communication with a site of excess body fluid within a patient; and the pressure reference assembly comprises:
a first reference line having a first portion and a second portion opposite the first portion, wherein the first portion of the first reference line has a first flexible region configured to sense pressure;
a second reference line having a first portion and a second portion opposite the first portion, wherein the first portion of the second reference line has a second flexible region configured to be in pressure communication with atmospheric pressure, wherein the second portions of the first and second reference lines are configured to be positioned at a second location spaced apart from the first and second flexible regions and; and
a pressure sensor assembly at the second portions of the first and second reference lines, wherein the pressure sensor assembly is configured to measure pressure and/or force at the second portions of the first and second reference lines.

10. The body fluid drainage system of claim 9, wherein the first and second reference lines are filled with a reference fluid.

11. The body fluid drainage system of claim 9, wherein the first and second flexible regions each comprise a flexible membrane made of an ether- and/or ester-based material.

12. The body fluid drainage system of claim 9, wherein the drainage catheter comprises a flexible interface member positioned distally with respect to the inlet and the first flexible region of the first reference line is configured to be in pressure communication with the flexible interface member of the drainage catheter.

13. The body fluid drainage system of claim 9, wherein the first flexible region of the first reference line is configured to be in pressure communication with atmospheric pressure.

14. The body fluid drainage system of claim 13, wherein the site of excess body fluid defines a point along a reference axis that extends through the site of excess body fluid; the first flexible region of the first reference line is configured to be positioned at a first location along the reference axis to one side of the inlet of the drainage catheter; and the second flexible region of the second reference line is configured to be positioned at a second location along the reference axis to a side of the inlet of the drainage catheter opposite the first flexible region.

15. The body fluid drainage system of claim 14, wherein the reference axis extends through lateral ventricles in a head of the patient, and wherein the first end portion of the first reference line is configured to be positioned on a first side of the head and the first end portion of the second reference line is configured to be positioned on a second side of the head opposite the first side.

16. The body fluid drainage system of claim 9, wherein the drainage catheter comprises a flexible interface member positioned distally with respect to the inlet and the flexible interface member and the first flexible region of the first reference line are attached together.

17. The body fluid drainage system of claim 9, wherein the drainage catheter comprises a flexible interface member positioned distally with respect to the inlet, and the flexible interface member and the first flexible region of the first reference line are positioned within a sealed compartment and are maintained in contact via a vacuum in the sealed compartment.

18. The body fluid drainage system of claim 9, wherein the drainage catheter comprises a flexible interface member positioned distally with respect to the inlet and the flexible interface member of the drainage catheter is outwardly biased.

19. The body fluid drainage system of claim 9, wherein the pressure sensor assembly is configured to measure intracranial pressure.

20. The body fluid drainage system of claim 18, wherein the flexible interface member is outwardly biased to maintain contact between the flexible interface member and the sensor when the flexible interface member is at negative pressures.

21. The body fluid drainage system of claim 20, further comprising a housing surrounding the flexible interface member and the flexible sensor membrane to define a sealed compartment, and wherein the flexible sensor membrane and the flexible interface member are placed in contact via a vacuum in the sealed compartment.

22. The body fluid drainage system of claim 9, wherein the drainage catheter additionally comprises a reservoir and at least one sensor positioned to detect when the reservoir is filled and drained.

23. The body fluid drainage system of claim 22, wherein the flow rate of fluid through the drainage catheter can be determined based on a known volume of the reservoir and the number of times the reservoir is filled or drained within a predetermined period of time.

24. The body fluid drainage system of claim 22, comprising at least one sensor that measures the fluid level at locations within the reservoir.

25. The body fluid drainage system of claim 22, wherein the reservoir is a drip chamber of known volume.

26. The body fluid drainage system of claim 22, wherein the reservoir additionally comprises a vent allowing air to enter and be displaced from the reservoir.

* * * * *